US011623084B2

United States Patent
Travers et al.

(10) Patent No.: US 11,623,084 B2
(45) Date of Patent: Apr. 11, 2023

(54) APPARATUS AND METHOD FOR TREATING MULTIPLE TUMORS IN PATIENTS WITH METASTATIC DISEASE BY ELECTRIC FIELDS

(71) Applicant: LifeBridge Innovations, PBC, Longwood, FL (US)

(72) Inventors: Peter F. Travers, Longwood, FL (US); Ken Watkins, Lake Mary, FL (US); Scott Krywick, Clermont, FL (US); Matthew Travers, Apopka, FL (US)

(73) Assignee: LifeBridge Innovations, PBC, Longwood, FL (US)

( * ) Notice: Subject to any disclaimer, the term of this patent is extended or adjusted under 35 U.S.C. 154(b) by 88 days.

(21) Appl. No.: 16/943,351

(22) Filed: Jul. 30, 2020

(65) Prior Publication Data

US 2020/0353245 A1 Nov. 12, 2020

Related U.S. Application Data

(60) Continuation of application No. 16/177,913, filed on Nov. 1, 2018, now abandoned, which is a
(Continued)

(51) Int. Cl.
*A61N 1/36* (2006.01)
*A61N 1/04* (2006.01)
(Continued)

(52) U.S. Cl.
CPC ....... *A61N 1/36002* (2017.08); *A61N 1/0476* (2013.01); *A61N 1/36014* (2013.01);
(Continued)

(58) Field of Classification Search
CPC ............ A61N 1/36002; A61N 1/36014; A61N 1/36185
See application file for complete search history.

(56) References Cited

U.S. PATENT DOCUMENTS 5,304,206 A * 4/1994 Baker, Jr. ........... A61N 1/37217
607/45
6,248,056 B1 6/2001 Persson
(Continued)

OTHER PUBLICATIONS

Notification of Transmittal of the International Search Report and the Written Opinion of the International Searching Authority, or the Declaration dated Oct. 16, 2015 for International Application No. PCT/US2015/040009 (11 pages).
(Continued)

*Primary Examiner* — Eric D. Bertram
(74) *Attorney, Agent, or Firm* — Taylor IP, P.C.

(57) ABSTRACT

An apparatus for delivering a plurality of electromagnetic fields to a body of an individual. The apparatus includes a plurality of electrode elements and a control device coupled with the plurality of electrode elements. The control device is configured to detect temperatures of the plurality of electrode elements, determine alternate firing sequences of the plurality of electrode elements, and implement the determined alternate firing sequences for delivering the plurality of electromagnetic fields for treating tumors in the body of the individual and reducing temperatures of the plurality of electrode elements.

10 Claims, 24 Drawing Sheets

Related U.S. Application Data continuation-in-part of application No. 15/826,112, filed on Nov. 29, 2017, now Pat. No. 10,675,460, which is a division of application No. 14/795,597, filed on Jul. 9, 2015, now Pat. No. 9,833,617.

(60) Provisional application No. 62/028,996, filed on Jul. 25, 2014.

(51) Int. Cl.
    *A61N 1/372* (2006.01)
    *A61N 1/40* (2006.01)
    *A61N 1/32* (2006.01)

(52) U.S. Cl.
    CPC ..... *A61N 1/36185* (2013.01); *A61N 1/37217* (2013.01); *A61N 1/40* (2013.01); *A61N 1/32* (2013.01)

(56) References Cited

U.S. PATENT DOCUMENTS

| | | |
|---|---|---|
| 6,443,978 B1 | 9/2002 | Zharov |
| 6,868,289 B2 | 3/2005 | Palti |
| 7,089,054 B2 | 8/2006 | Palti |
| 7,146,210 B2 | 12/2006 | Palti |
| 8,019,414 B2 | 9/2011 | Palti |
| 8,185,213 B2 | 5/2012 | Kveen et al. |
| RE43,618 E | 8/2012 | Palti |
| 8,406,870 B2 | 3/2013 | Palti |
| 8,465,533 B2 | 6/2013 | Palti |
| 8,706,261 B2 | 4/2014 | Palti |
| 2003/0097152 A1 | 5/2003 | Palti |
| 2005/0209640 A1* | 9/2005 | Palti ................ A61N 1/326 607/2 |
| 2006/0149341 A1* | 7/2006 | Palti ................ A61N 1/0492 600/372 |
| 2007/0255269 A1* | 11/2007 | Shin ................ A61B 18/1206 606/34 |
| 2008/0097530 A1 | 4/2008 | Muccio et al. |
| 2008/0188846 A1 | 8/2008 | Palanker et al. |
| 2009/0076366 A1* | 3/2009 | Palti ................ A61N 1/0408 600/395 |
| 2012/0184800 A1 | 7/2012 | Brighton |
| 2013/0184637 A1 | 7/2013 | Palti |
| 2013/0184674 A1 | 7/2013 | Palti |
| 2013/0296995 A1 | 11/2013 | Mahmood et al. |
| 2014/0148872 A1 | 5/2014 | Goldwasser et al. |
| 2017/0224990 A1 | 8/2017 | Goldwasser et al. |
| 2018/0085575 A1 | 3/2018 | Travers et al. |

OTHER PUBLICATIONS

Notification of Transmittal of the International Search Report and the Written Opinion of the International Searching Authority, or the Declaration dated Dec. 2, 2019 for International Application No. PCT/US2019/045829 (16 pages).

* cited by examiner

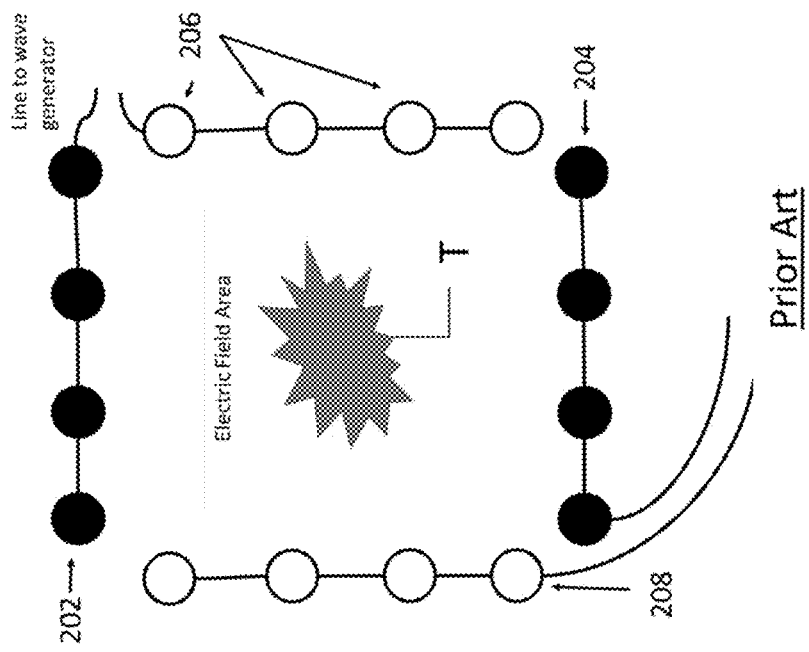
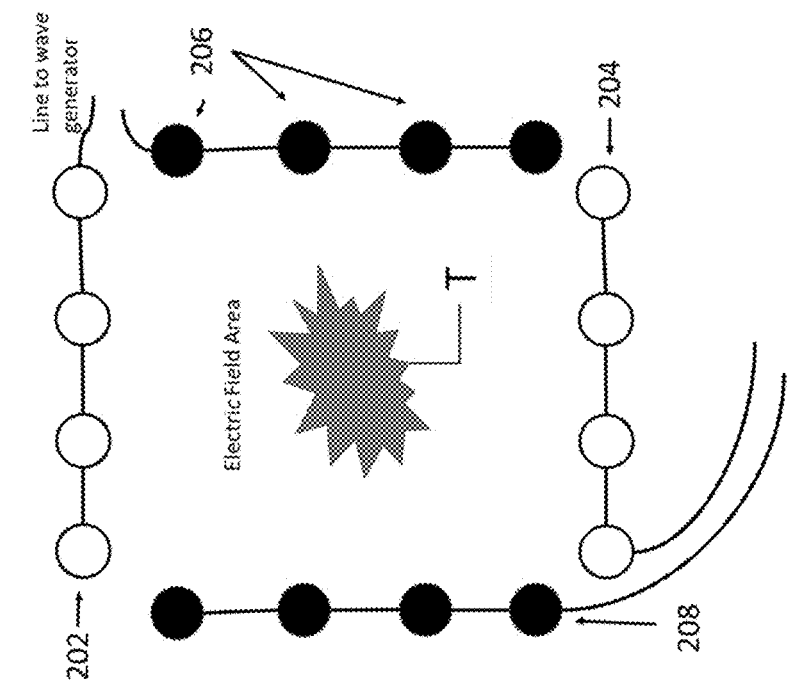

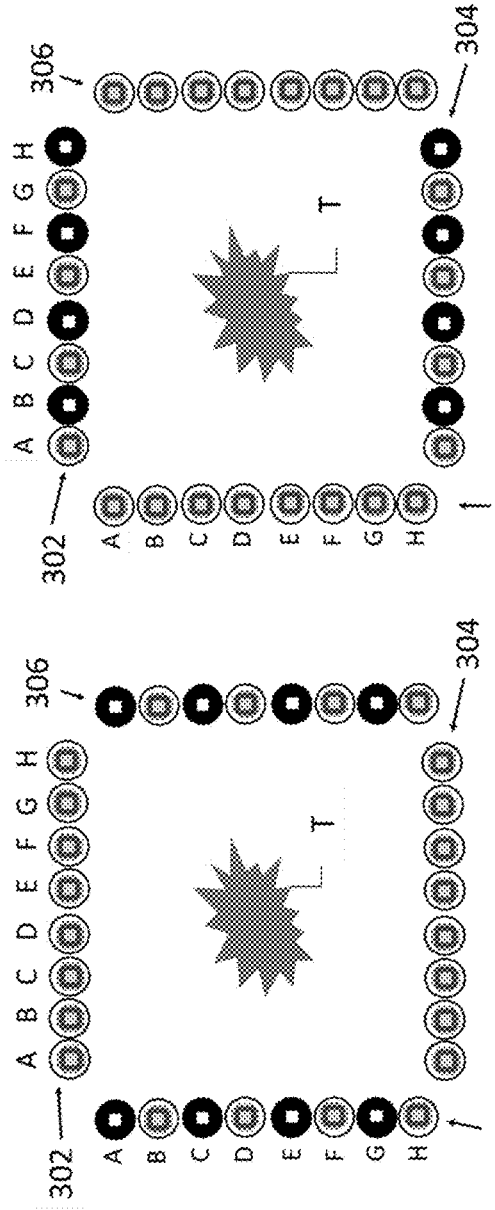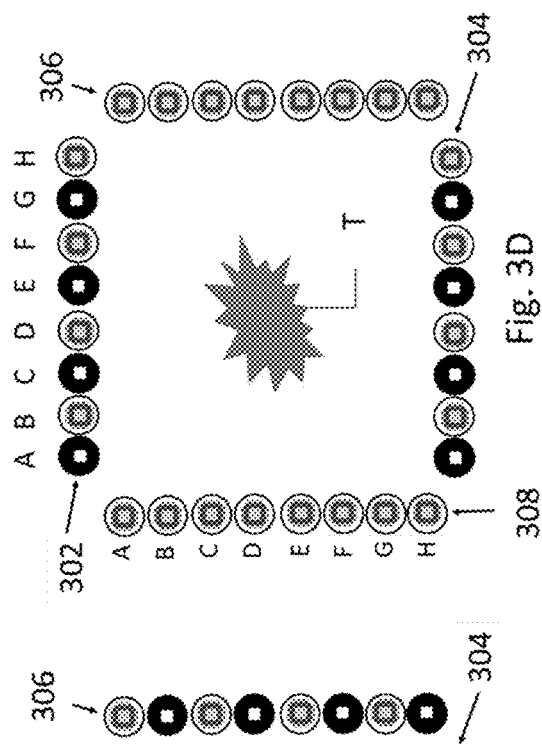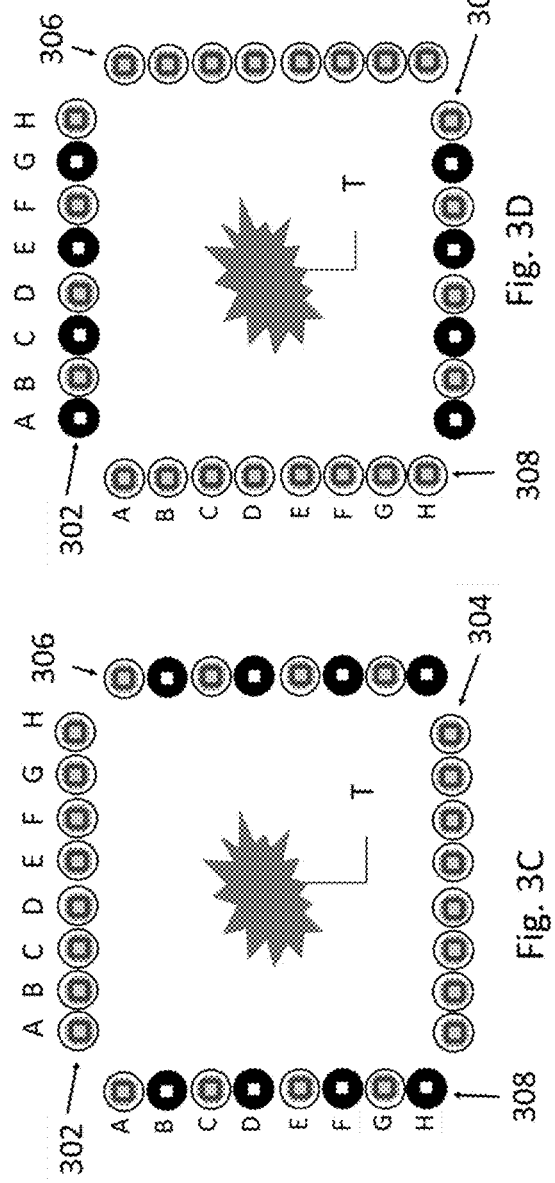
Fig. 3A  Fig. 3B  Fig. 3C  Fig. 3D

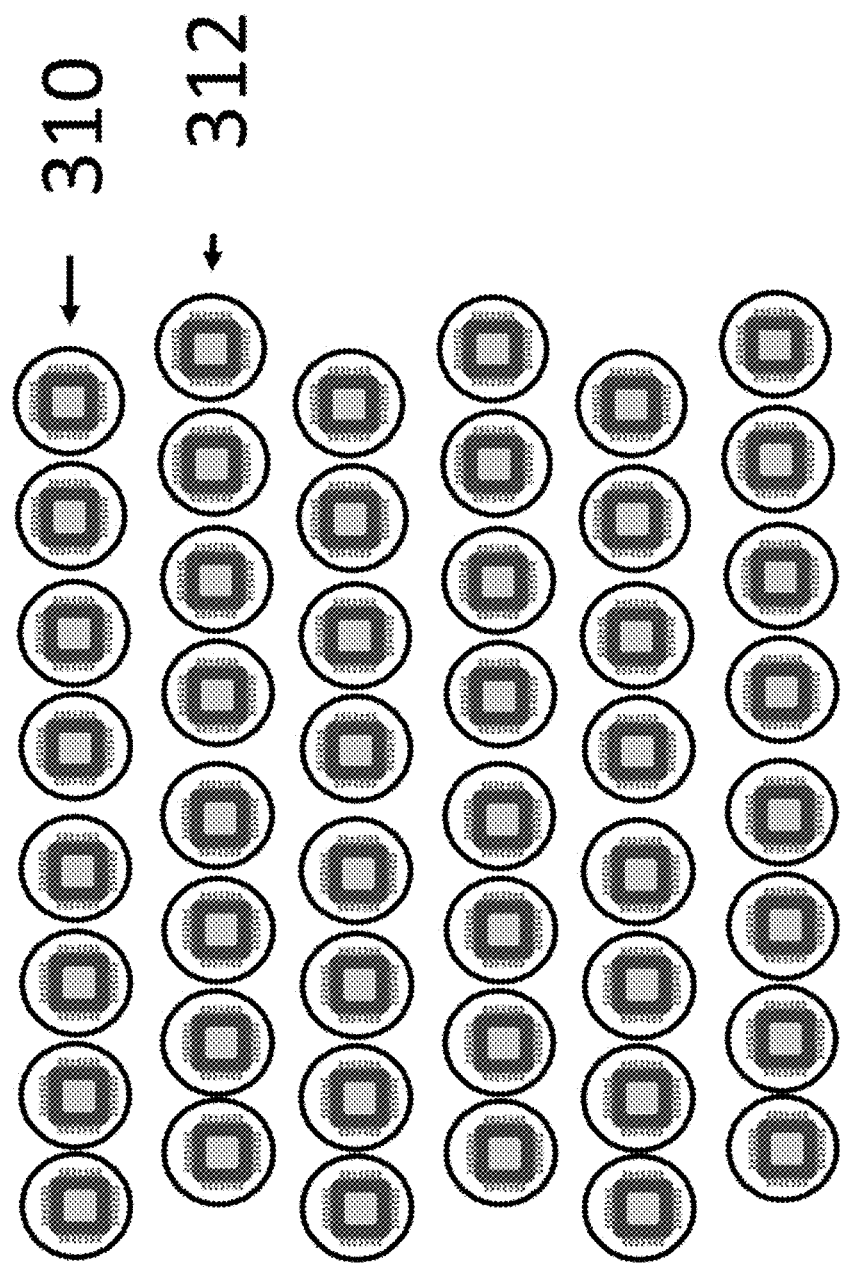

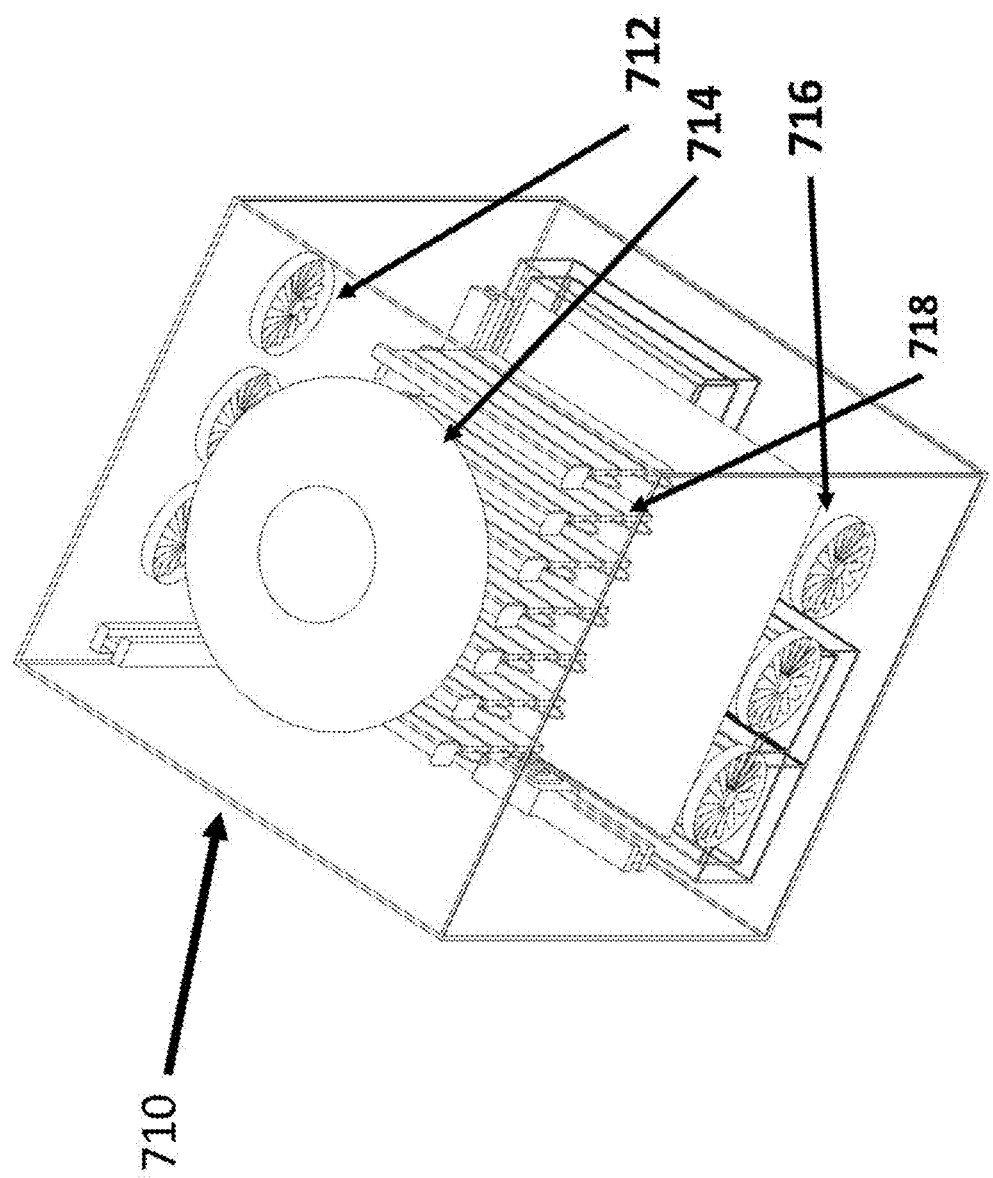

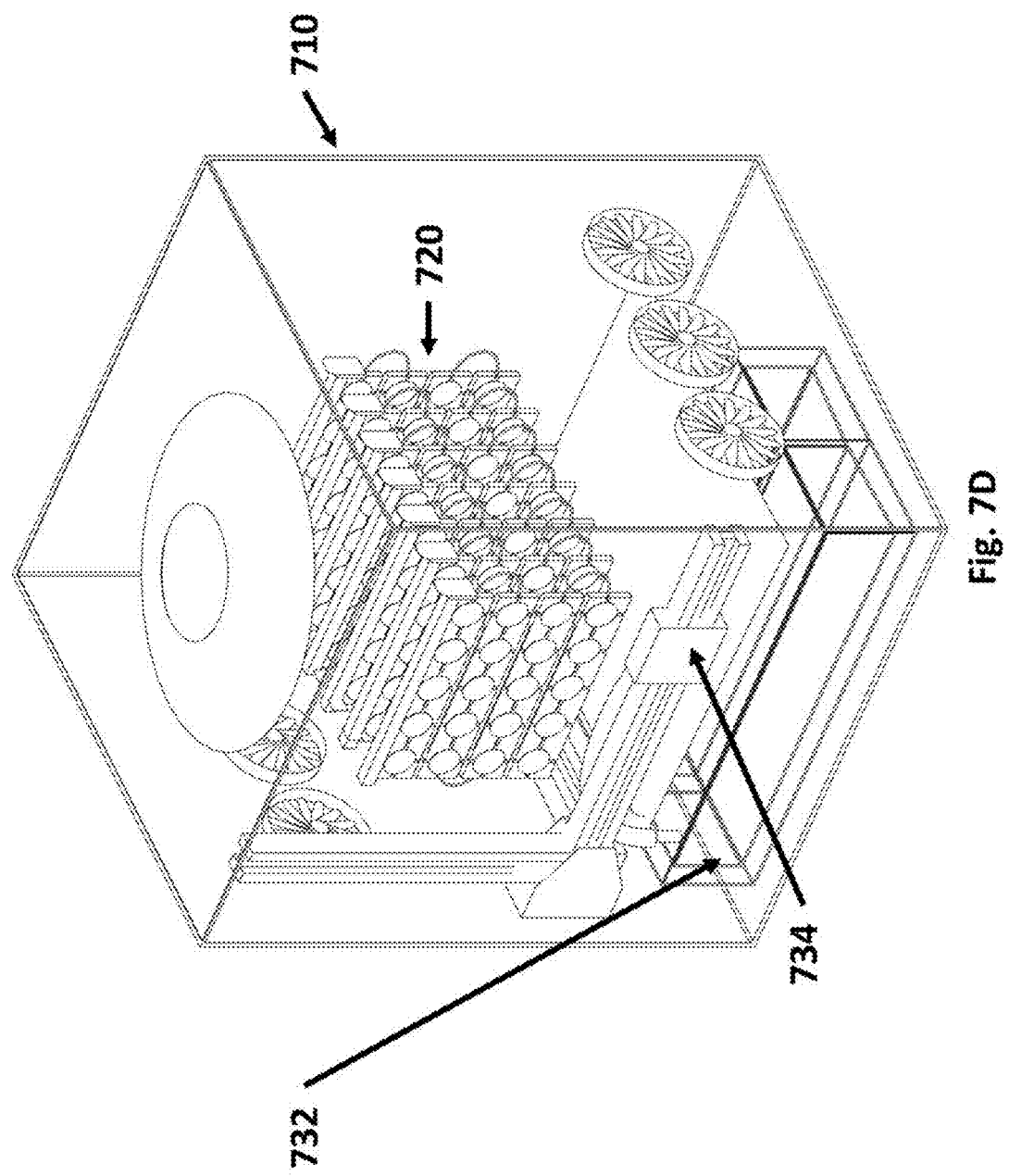

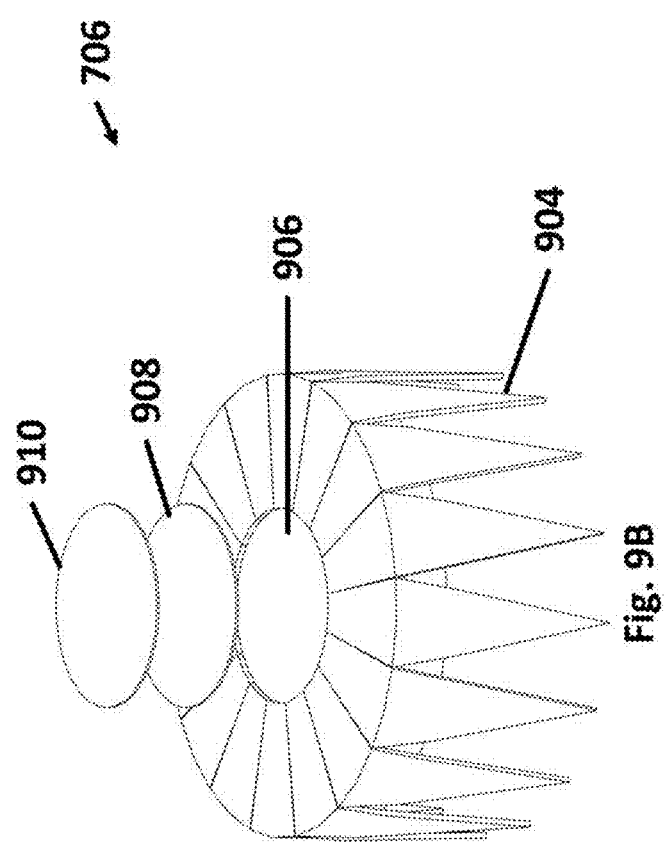

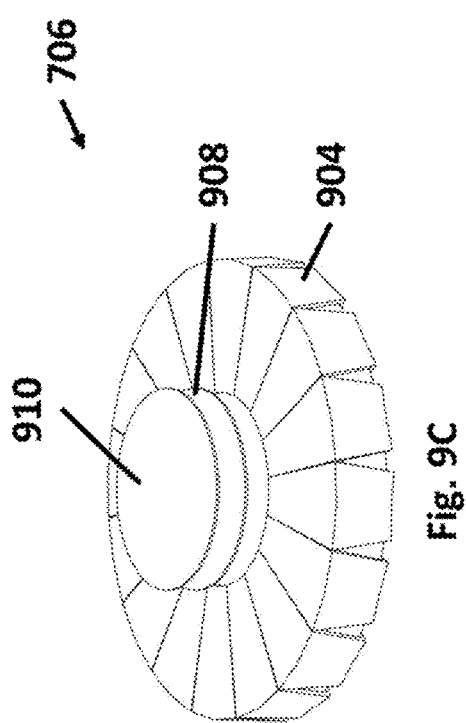

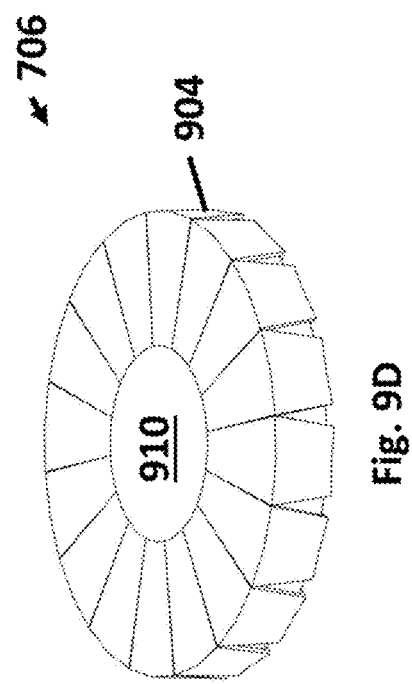

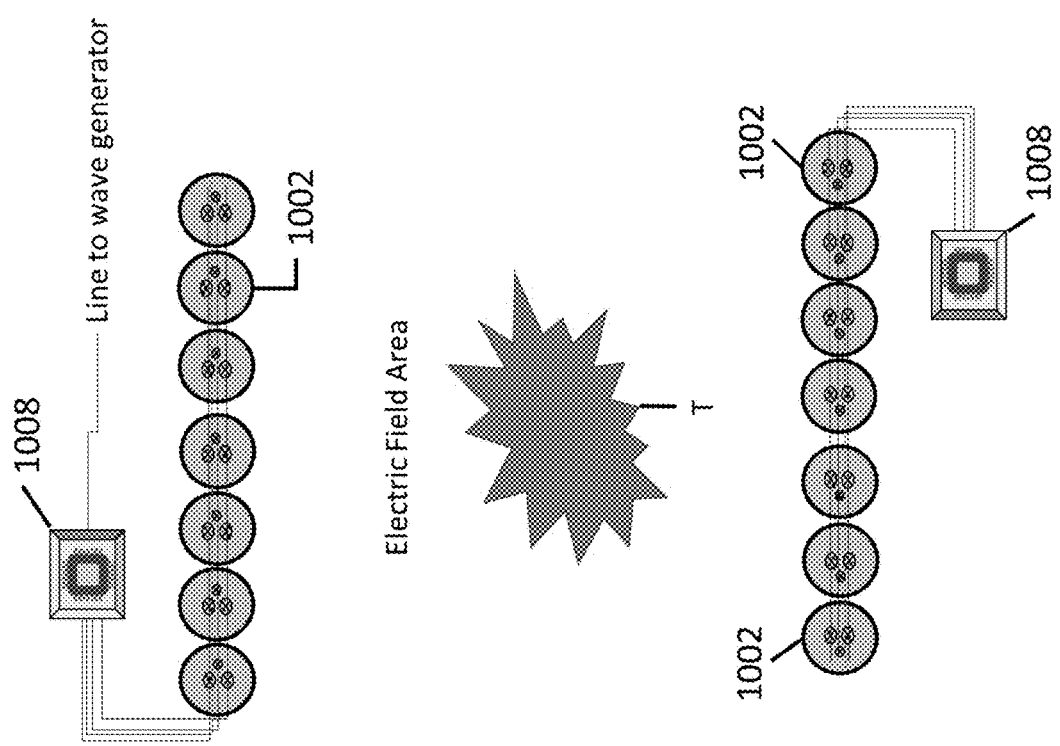

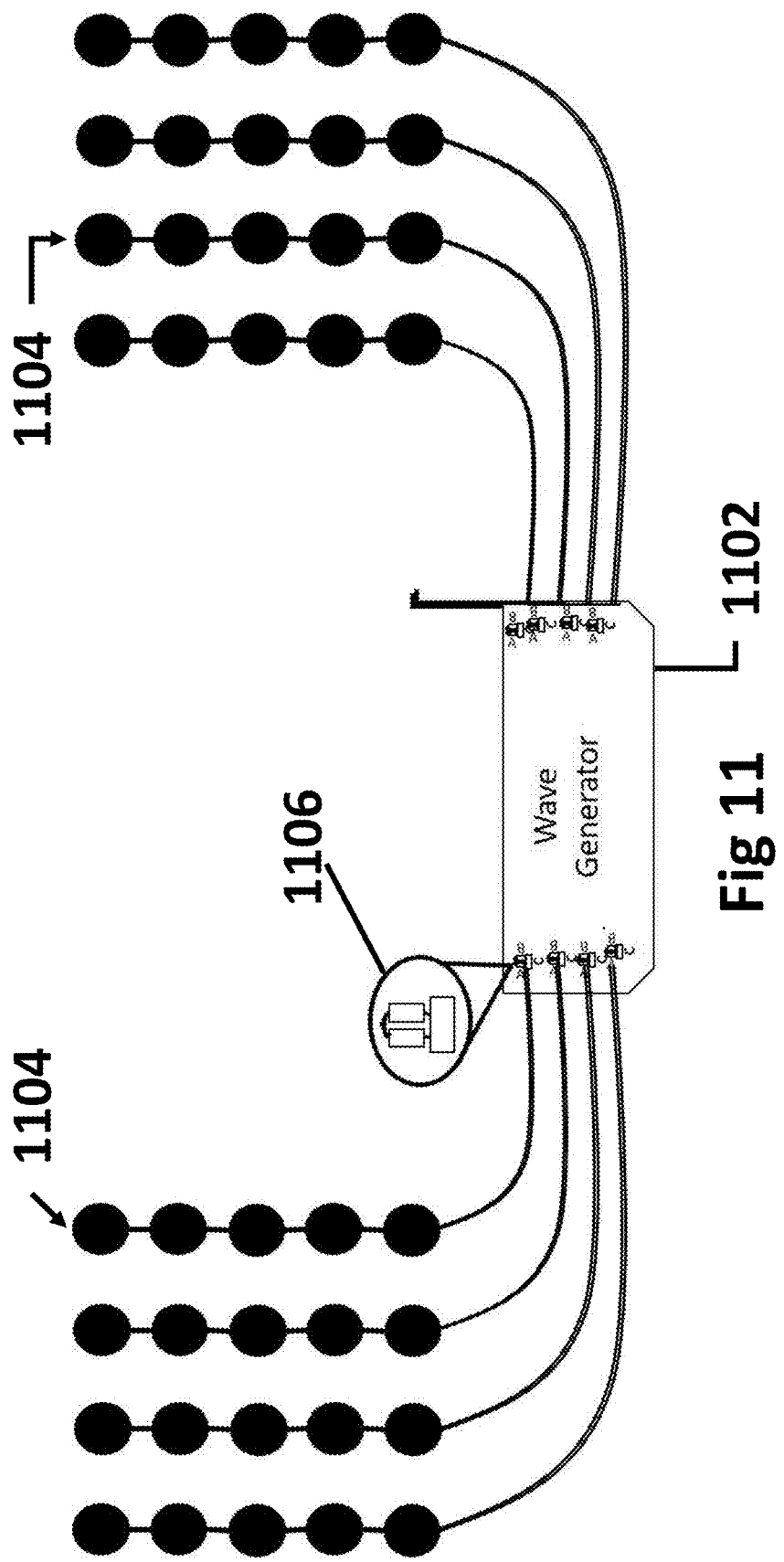

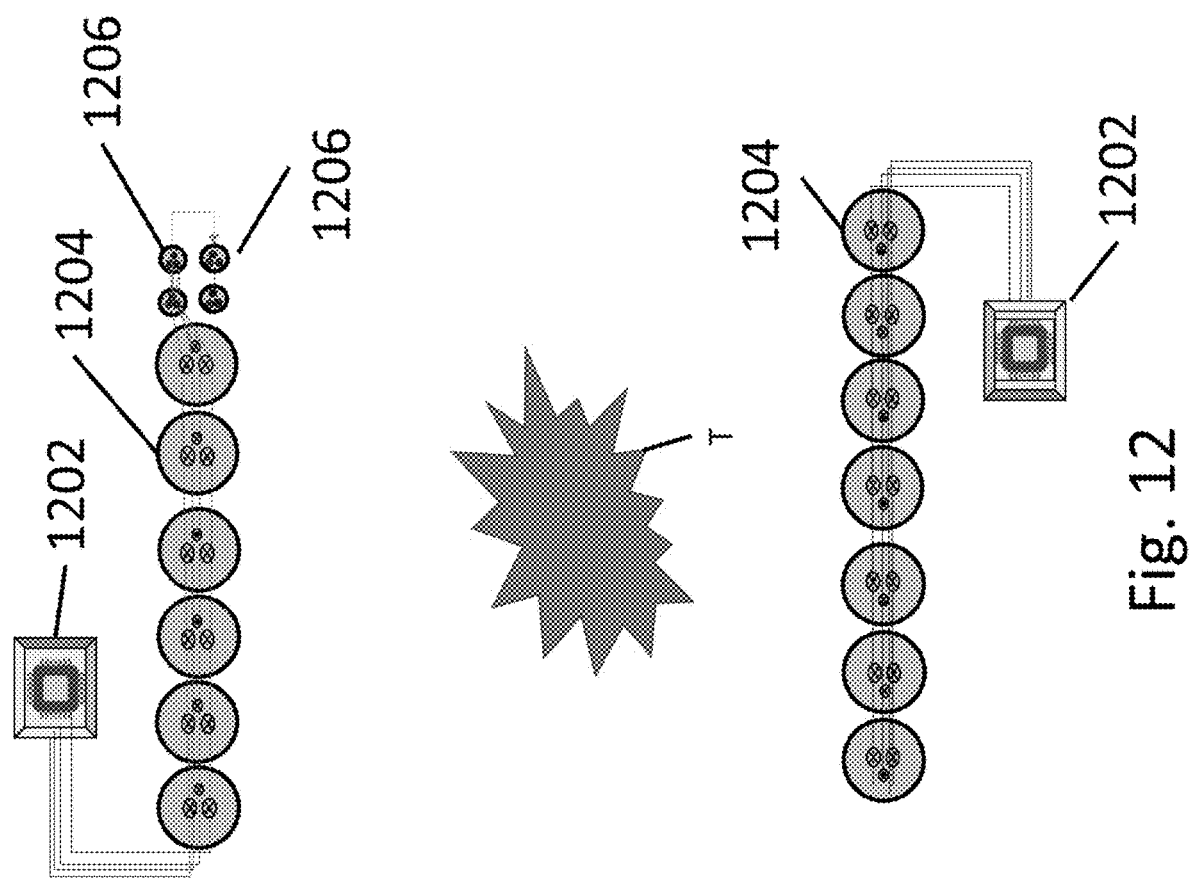

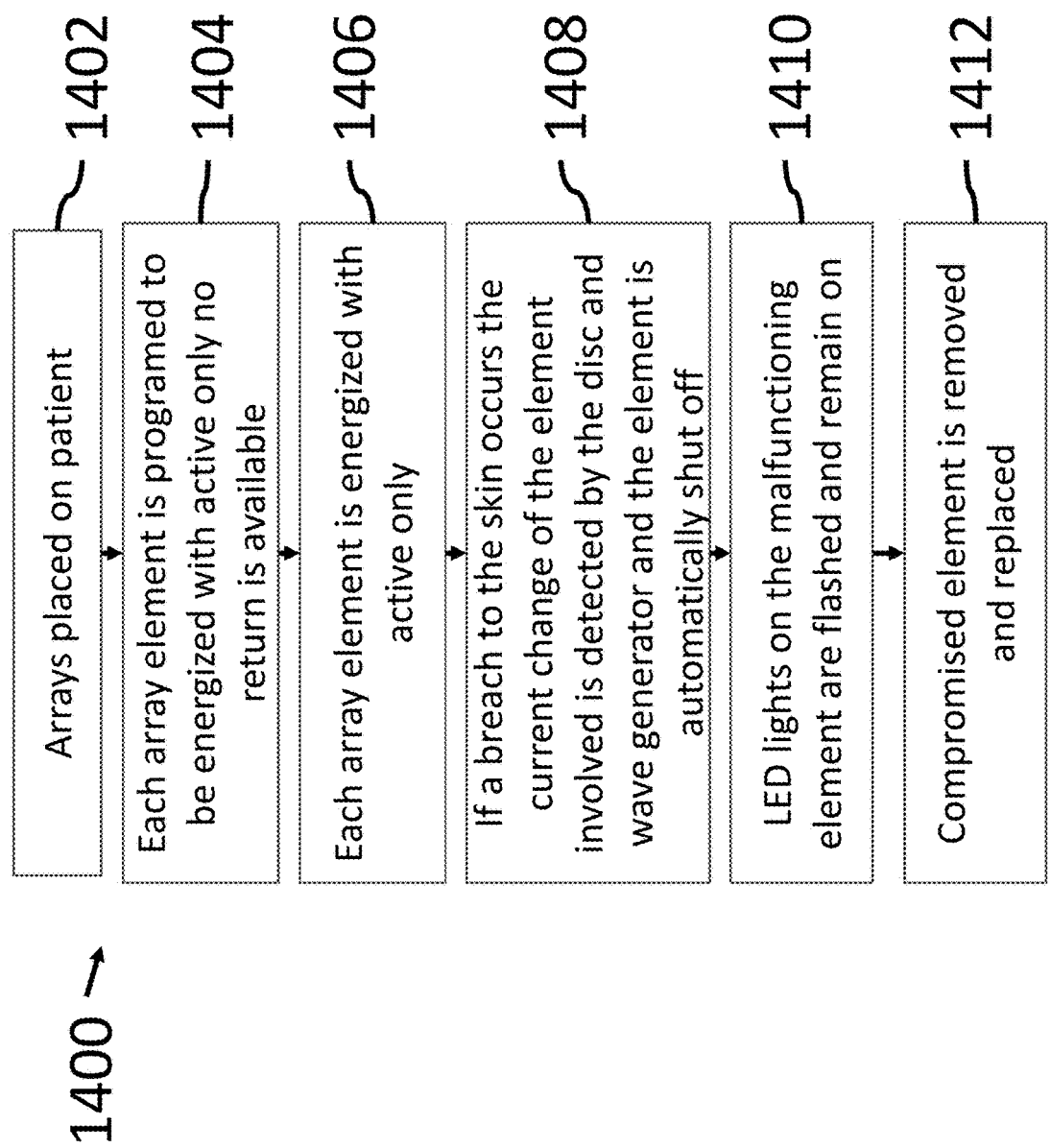

APPARATUS AND METHOD FOR TREATING MULTIPLE TUMORS IN PATIENTS WITH METASTATIC DISEASE BY ELECTRIC FIELDS

CROSS REFERENCE TO RELATED APPLICATIONS

This is a continuation application of U.S. non-provisional patent application Ser. No. 16/177,913, entitled, "APPARATUS AND METHOD FOR TREATING MULTIPLE TUMORS IN PATIENTS WITH METASTATIC DISEASE BY ELECTRIC FIELDS", filed Nov. 1, 2018, which is incorporated herein by reference. U.S. non-provisional patent application Ser. No. 16/177,913 is a continuation-in-part application based upon U.S. non-provisional patent application Ser. No. 15/826,112, entitled "APPARATUS AND METHOD FOR TREATING MULTIPLE TUMORS IN PATIENTS WITH METASTATIC DISEASE BY ELECTRIC FIELDS", filed Nov. 29, 2017, which has now issued as U.S. Pat. No. 10,675,460, and which is incorporated herein by reference. U.S. non-provisional patent application Ser. No. 15/826,112 is a divisional application based upon U.S. non-provisional patent application Ser. No. 14/795,597, entitled "APPARATUS AND METHOD FOR TREATING MULTIPLE TUMORS IN PATIENTS WITH METASTATIC DISEASE BY ELECTRIC FIELDS", filed Jul. 9, 2015, which has now issued as U.S. Pat. No. 9,833,617, and which is incorporated herein by reference. U.S. non-provisional patent application Ser. No. 14/795,597 is based upon U.S. provisional patent application Ser. No. 62/028,996, entitled "APPARATUS AND METHOD FOR TREATING MULTIPLE TUMORS IN PATIENTS WITH ADVANCED METASTATIC DISEASE BY ELECTRIC FIELDS", filed Jul. 25, 2014, which is incorporated herein by reference.

BACKGROUND OF THE INVENTION

1. Field of the Invention

The present invention relates to tumor and cancer cell treatment and more specifically to treatments involving the application of electromagnetic fields.

2. Description of the Related Art

Alternating Electric Fields, also referred to as Tumor Treating Fields (TTF's), can be employed as a type of cancer treatment therapy by using low-intensity electromagnetic fields. These low-intensity fields rapidly change direction, thousands of times per second. Since the TTF's are electric fields, they do not cause muscle twitching or severe adverse side effects on other electrically activated tissues. The growth rate of metastatic diseases is typically greater than the growth rate of normal, healthy cells. Alternating Electric Fields therapy takes advantage of this high growth-rate characteristic. TTF's act to disrupt a cancer cell's mitotic process and cytokinesis by manipulating the cell's polarizable intracellular constituents, namely tublins that form mitotic spindles that pull the genetic material in the nucleus into two sister cells. TTF's interrupt mitotic spindle microtubule assembly thereby preventing cell division. The metastatic disease cells treated using TTF's will go into programmed cell death usually within 4 to 5 hours. The result is a significant reduction in tumor size and potential for full elimination of solid tumors. TTF's are tuned to treat specific cancer cells and thereby do not damage normal cells. TTF therapy can be used as a sole treatment method, or it can be combined with conventional drug delivery mechanisms.

TTF's are applied to patients using insulated electrodes adhered to the skin by a variety of methods including the use of medical adhesives, articles of clothing, etc. There are multiple configurations of insulated electrodes, but all have an insulated material with a high dielectric constant on one side and a thin metal coating on the other, usually silver. Insulated electrodes used to generate TTF's always come in pairs with both sides being similar, but not necessarily the same.

What is needed in the art, is a TTF system that enables the dynamic reassignment of array elements to thereby define any array needed and to apply the field from selected electrode elements.

What is needed in the art is a modular system for adding and removing array elements.

What is needed in the art is a current monitoring sensor that sends a shut off signal to the control device if fluctuations in current, which may be caused by current leakage to the skin or the detachment of the electrode, is detected.

What is needed in the art is a method of adhering array elements to a material while also reducing the temperature of the array elements.

SUMMARY OF THE INVENTION

The present invention provides an improved cancer and tumor treatment regime.

The invention in one form is directed to an apparatus for delivering a plurality of electromagnetic fields to a body of an individual. The apparatus includes a plurality of electrode elements configured for being located on the body of the individual. The apparatus may also include a support material configured for holding the plurality of electrode elements relative to the body of the individual. The apparatus also includes a control device coupled with the plurality of electrode elements. The control device is configured to detect temperatures of the plurality of electrode elements, determine alternate firing sequences of the plurality of electrode elements, and implement the determined alternate firing sequences for delivering the plurality of electromagnetic fields for treating tumors in the body of the individual and reducing temperatures of the plurality of electrode elements.

The invention in another form is directed to a method for delivering a plurality of electromagnetic fields to a body of an individual. The method includes the steps of locating a plurality of electrode elements on the body of the individual and detecting temperatures of the plurality of electrode elements. The method also includes the step of determining alternate firing sequences of the plurality of electrode elements. The method also includes the step of implementing the determined alternate firing sequences for delivering the plurality of tumor treating electromagnetic fields and reducing temperatures of the plurality of electrode elements.

An advantage of the present invention is that connected sets of master and slave electrode elements are used to deliver programmed electric signals to selected electrodes attached to the patient. The arrangement of which reduces the cost of the electrode arrays.

Another advantage of the present invention is that it allows for less warming of a patient's skin from individual electrodes.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 2A illustrates a firing of selected array elements of prior art systems;

FIG. 2B illustrates a firing of another selection of array elements by a prior art system;

FIG. 3A illustrates a firing of individual programmable array elements of an array of elements to treat a tumor in a patient of the present invention, using the method of FIG. 1;

FIG. 3B illustrates a firing of other individual programmable array elements of the array of elements of FIG. 3A;

FIG. 3C illustrates a firing of still other individual programmable array elements of the array of elements of FIGS. 3A and 3B;

FIG. 3D illustrates a firing of yet still other individual programmable array elements of the array of elements of FIG. 3A-3C;

FIG. 3E illustrates sub-arrays of individual programmable array elements;

FIG. 7B illustrates a device used to clean and apply adhesive to the electrode elements;

FIG. 7D illustrates the nozzle directing device to clean and apply adhesive to the electrode elements held in retaining racks;

FIG. 9B further illustrates the making of an electrode;

FIG. 9C still further illustrates the making of an electrode;

FIG. 9D yet still further illustrates the making of an electrode;

FIG. 10B illustrates another coupling of the field generator to a subarray of electrodes;

FIG. 11 illustrates an embodiment of the present invention in which each electrode element is coupled to the field/wave generator;

FIG. 12 is a diagram illustrating another embodiment in which signals from the field generator are coupled to the electrodes;

FIG. 14 presents another method of the present invention; and

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
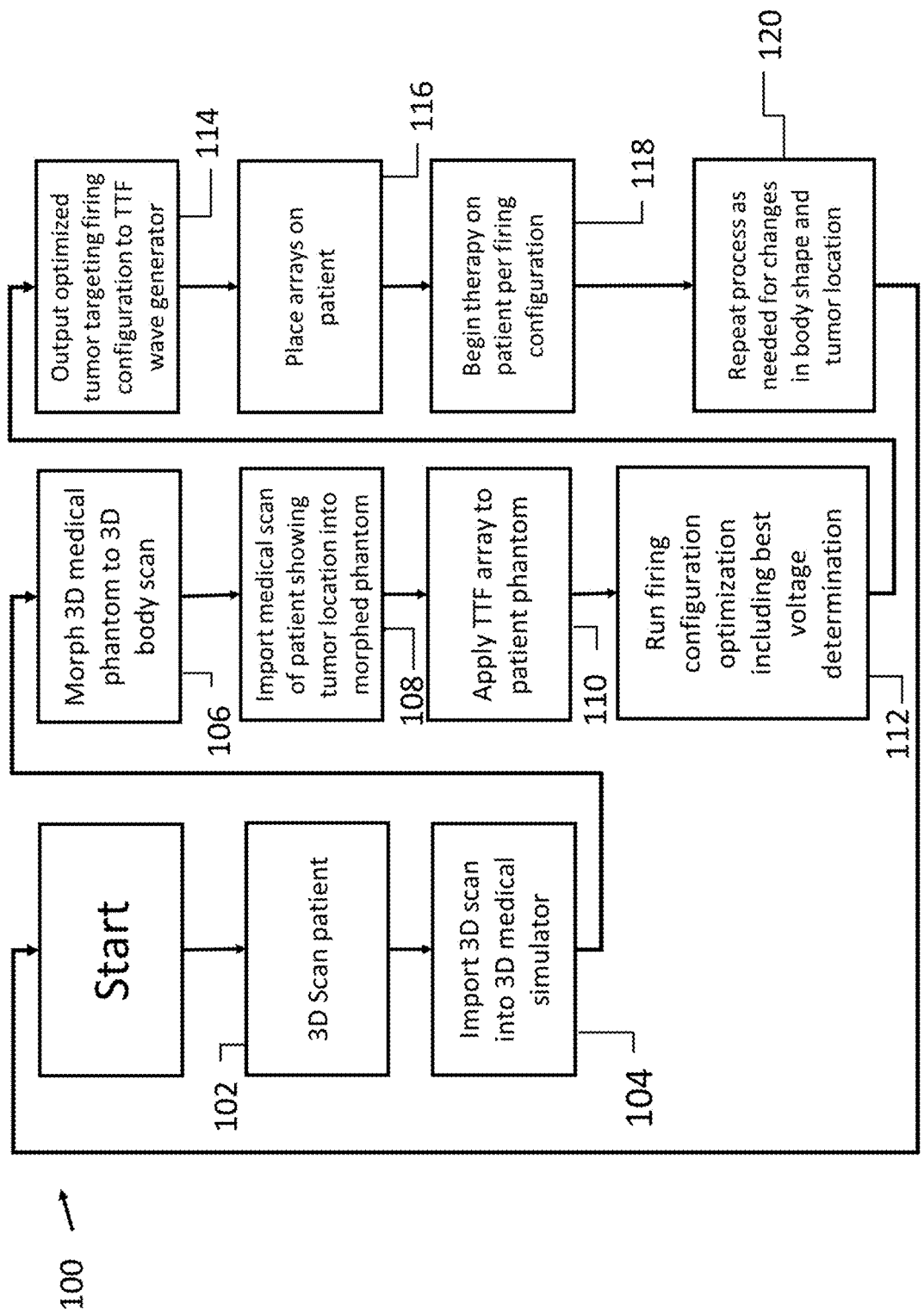
FIG. 1 is a flowchart illustrating an embodiment of a treatment method of the present invention.

Referring to the drawings and more particularly to FIG. 1 there is illustrated an embodiment of a treatment method 100 of the present invention for preparing to treat a patient. One important step in administering tumor treating fields (TTF) is positioning electric fields to target multiple tumors in the human body. The present invention uses a process for optimizing the placement of array elements on the body as well as an optimal firing sequence for the array elements, to take advantage of the placement of the elements. First at step 102, a 3-D scan is made of the entire patient's body or at least a portion that includes the tumors to be treated. This 3-D scan is then imported into a medical simulator like Sim4life, at step 104. These medical simulators have phantoms or avatars that meet general body types of most of the population. The phantoms are 3-D bodies with all tissue types and organs simulating the human anatomy. An appropriate 3-D phantom is selected to match the imported 3-D model of our patient and the patient model is morphed to the phantom, at step 106. At step 108, the patient's medical scans such as PET scans or CT scans are imported into the morphed phantom matching our patient. The result is a medical simulation of our patient with tumors in the correct location. At step 110, the medical simulator is used to add TTF arrays to the simulated 3-D patient. At step 112, a simulated firing algorithm is run, analyzing which sequence or combination of array elements optimally treats the tumors in the simulation. The behavior of electric fields from the TTF is simulated through the body tissues and organs to evaluate the effectiveness of the applied electromagnetic fields and to optimize the firing sequence at step 114. The results of the optimal firing sequence are then exported to the wave generator. At step 116 the arrays are placed on the patient accordingly and treatment begins at step 118 using the firing sequence sent to the wave generator. When needed the process is repeated (step 120) for changes in body shape from loss or gaining of weight and or the development of new tumors.

A significant problem when administering TTF is the production of heat at the electrode site that can minimize the effectiveness of the treatment. It is well known by those experienced in the field that the intensity of the electromagnetic field administered through TTF has a significant effect on how well it reduces tumors. Electric fields at the appropriate frequency traveling through a tumor at 1V/cm reduces tumor growth but may not eliminate the tumor. The same electric field at 2V/cm to 3V/cm is much more likely to fully eliminate cells in a target tumor. However, electric fields at the 2V/cm to 3V/cm intensities can produce warmth on the array elements on the skin of the patient that cannot be tolerated. Indeed, the present form of an FDA approved device is programmed to reduce intensity when array elements reach 105.8 degrees Fahrenheit. This heating and the subsequent reduction in field intensity makes the therapy less effective.

The present invention overcomes this issue in part by minimizing the duty cycle of array elements. This is accomplished by individually controlling each array element and generally places more discs per square inch on the body than prior art forms of TTF which only control groups of array elements. For example, now additionally referring to FIGS. 2A and 2B, prior art TTF devices may have arrays 202, 204, 206, 208 comprised of 5 rows of 4 discs (only one row of each being illustrated) placed 3 inches on center over the front of the chest (array 202) and the same on the back (via array 204), for the treatment of tumor T. The illustrations have a single row of elements, for the sake of simplicity in illustrating, in straight rows, while it is to be understood that the arrays are actually positioned on the surface of the body. This pair of arrays is accompanied by a similar pair 206, 208 on the sides of the body left and right. The typical firing sequences is front-to-back then side-to-side. This places each array on a 50% duty cycle (as illustrated in FIGS. 2A and 2B) producing a significant amount of warming of array elements that must be managed by turning down electric field intensity levels.

Now, additionally referring to FIGS. 3A-3D, in contrast to the prior art, the present invention uses nearly twice the number of array elements over the same area front-to-back and side-to-side. FIGS. 3A-3D include arrays 302, 304, 306 and 308, each with individual references to elements A-H. Again, although shown schematically in two dimensions with single rows of elements, the arrays themselves have rows and columns of elements that are placed on the surface contours of a body, providing a three dimensional positioning of the elements. Since each element can be independently and dynamically controlled it is possible to produce firing sequences that target a given area alternating array elements. From a macro perspective, this can produce the desired field with a 25% duty cycle on the array elements making it less likely they will warm to undesirable temperatures enabling sustained higher field intensities to more likely eliminate tumor T by preventing the cells therein from successfully dividing. This is illustrated in FIGS. 3A-3D by showing elements that are darker as being the selected elements that are used in each particular figure. Beyond the wider view of reducing the duty cycle of an element, the individual control of elements allow the ability to maintain desired field strengths in tumor T by knowing the relative positions of each element of each array, so that the wave generator can select elements that will be used in a selected sequence for maintaining optimal field strength in the targeted area of tumor T. For example, the wave generator may select elements 308G and 302H to produce an electric field therebetween based on the information gained in steps 102-114 of method 100. Whereas the present invention has 3-D information about the location and shape of tumor T, the selection of particular elements of the arrays 302, 304, 306, 308 can be done to ensure that the electromagnetic field strength in and slightly around tumor T can be maintained, while the field strength in other parts of the body may be of a reduced magnitude. To help minimize the duty cycle of array elements they may be placed in strategic placements, not just parallel rows. For example, FIG. 3E shows array placement in offset rows (310-312) which may be more likely to minimize a change in placement of TTF fields when switching from one row to the next. Such strategic placement of array elements is included in simulation algorithms discussed herein.

Figure 4:
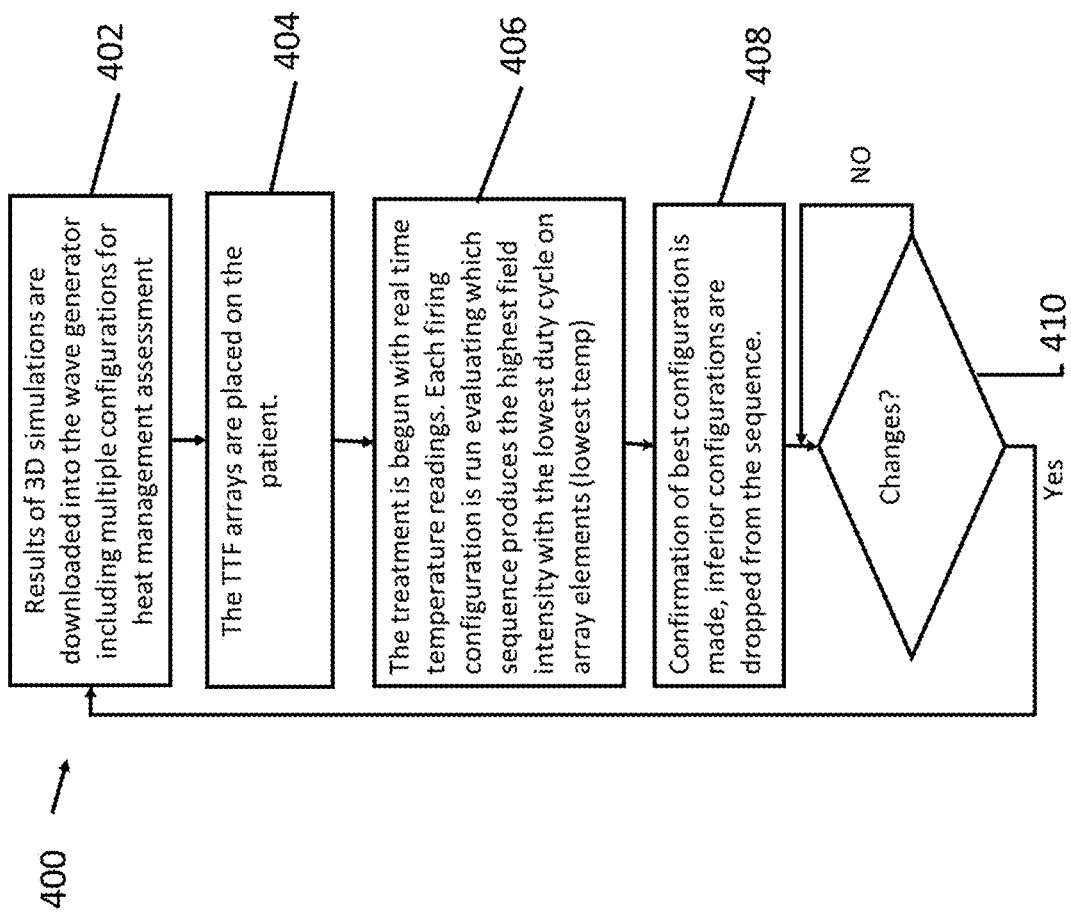
FIG. 4 is a flowchart of steps of another embodiment of a treatment process of the present invention.

Now, additionally referring to FIG. 4, there is illustrated a flowchart embodying a method 400. Method 400 determines the best firing sequence to manage warmth and field intensity. The 3-D simulation process is run to include multiple alternating firing sequences to produce the same essential electric field coverage required to target the patient's tumors (see step 116). At step 402 this information is downloaded into the wave generator. The TTF arrays 302, 304, 306, 308 are then placed on the patient at step 404. Heat sensors on each array element provide real time feedback and field intensity monitoring. The various firing sequences are run and monitored in step 406. The sequences that provide the highest field intensity within temperature parameters are chosen for treatment and the other sequences are dropped in step 408. Thereby producing the most tumor reduction per hour of use and if changes are needed (step 410) method 400 is repeated.

Figure 5:
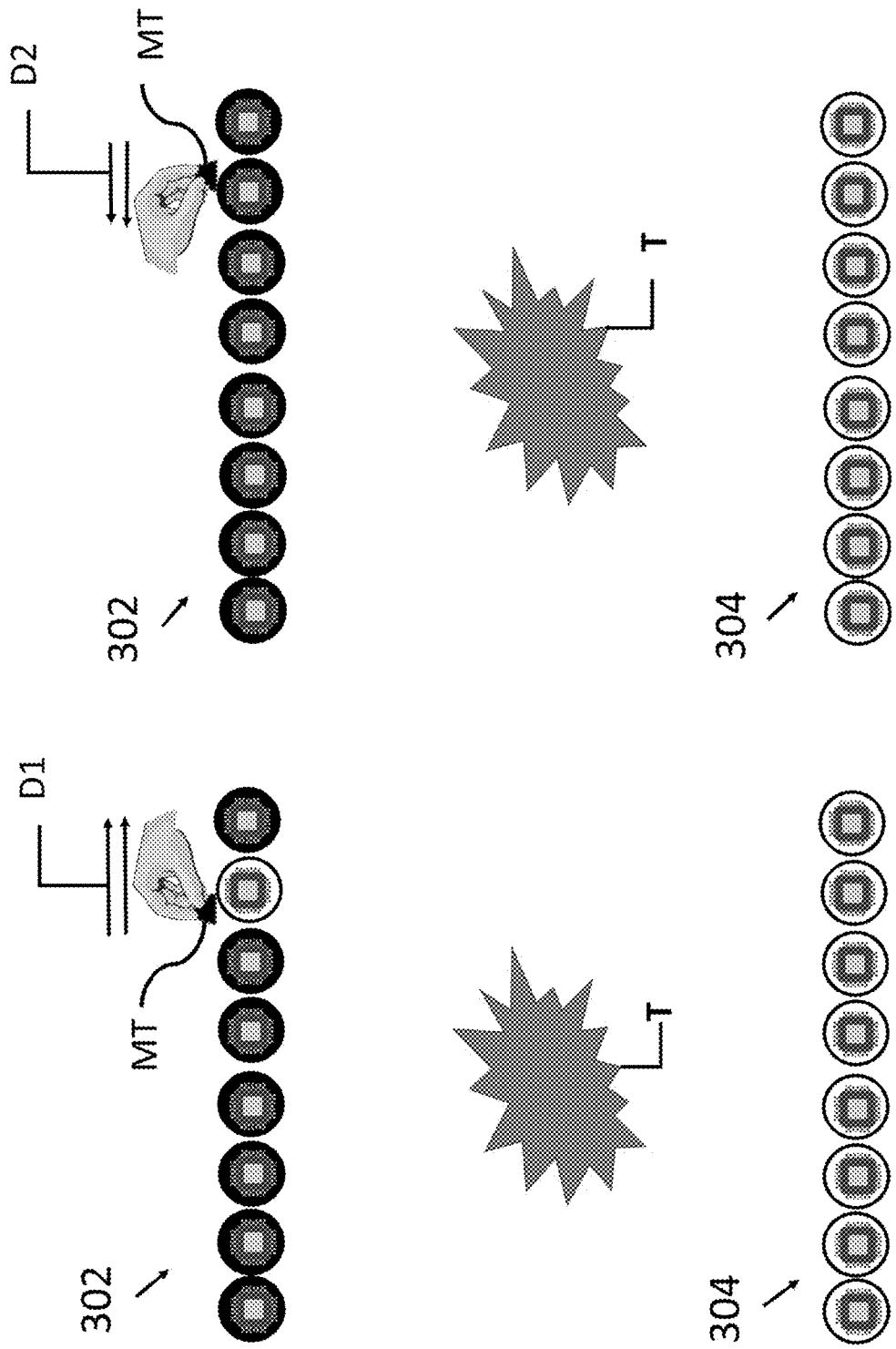
FIG. 5A illustrates an embodiment of a method of deactivating a selected array element of the present invention.
FIG. 5B illustrates an embodiment of a method of activating a selected array element of the present invention.

Regardless of the guidance provided by 3-D simulation in positioning array elements for TTF on a patient's body, actual application will require adjustments. This can occur for many reasons, such as a change in the patient's weight, that has not yet been compensated for by re-running the 3-D simulation, the occurrence of peripheral nerve stimulation in isolated spots on the abdomen, or difficult to correct errors in placement with medical adhesives. The present invention provides for individual array elements to be turned on and off to adjust for such occurrence without having to adjust entire arrays. This is accomplished by identifying the address of an array element and making a computer entry to selective turn off and on array elements, which may be a somewhat tedious task. To streamline this process the present invention provides for the use of a magnetic tool MT that is swept over the top of an array element in close proximity. The magnetic tool MT interacts with sensors built into the array elements and removes the element from active duty (see FIG. 5A) or enters it into active duty (See FIG. 5B) depending on the need. The magnetic tool MT is directional in that sweeping in one direction, say left to right, as in FIG. 5A in direction D1, removes an element from active duty and right to left, as in FIG. 5B in direction D2, enters it into active duty. It is also contemplated to educate the patient to enable/disable some elements using this method if particular elements seem problematic to the patient. It is contemplated that the wave generator will compensate for the enabled/disable elements so that effective treatment continues in light of the reconfigured elements.

Figure 6:
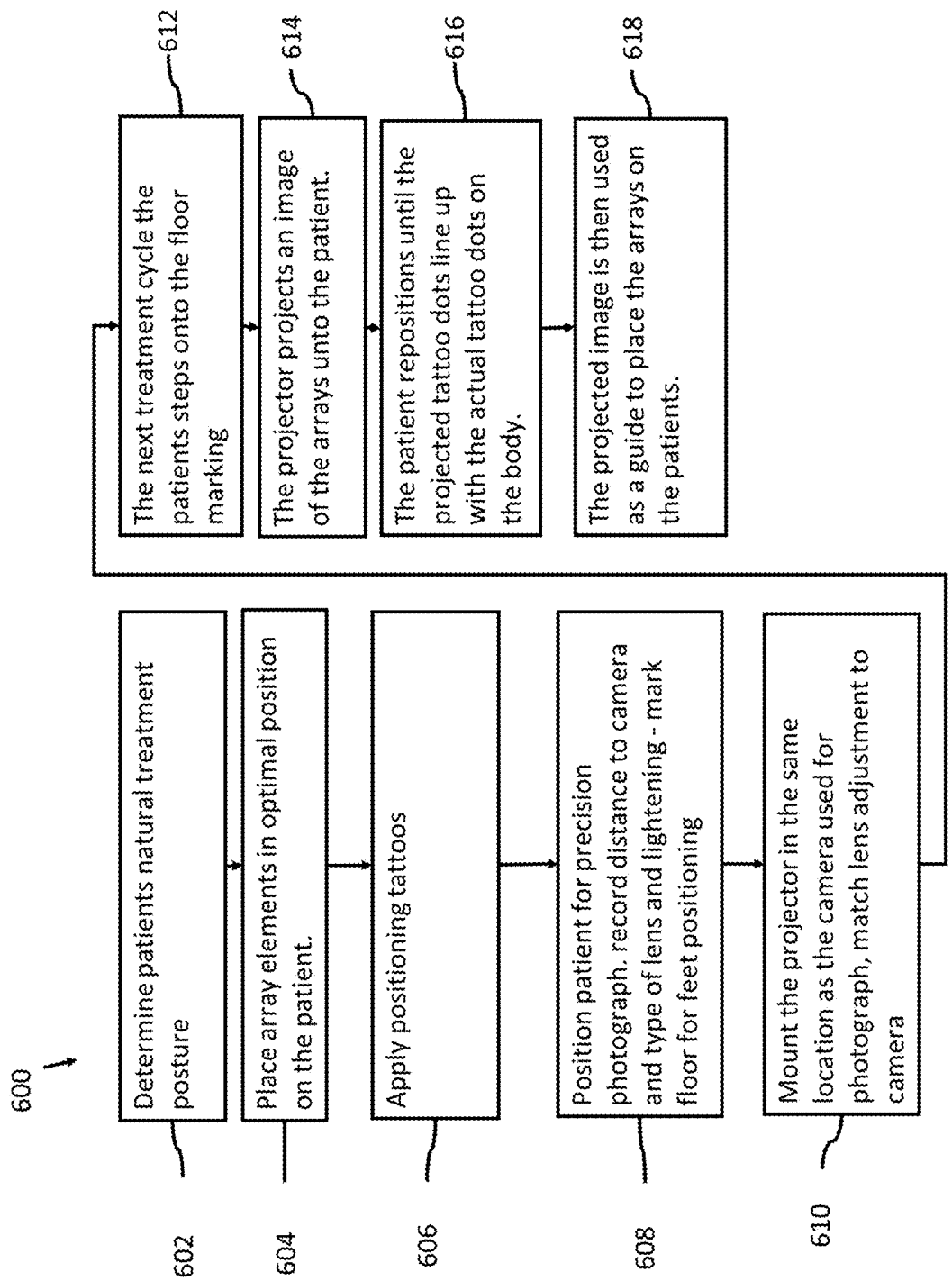
FIG. 6 is a flowchart illustrating an embodiment of a treatment method of the present invention.
Figure 7A:
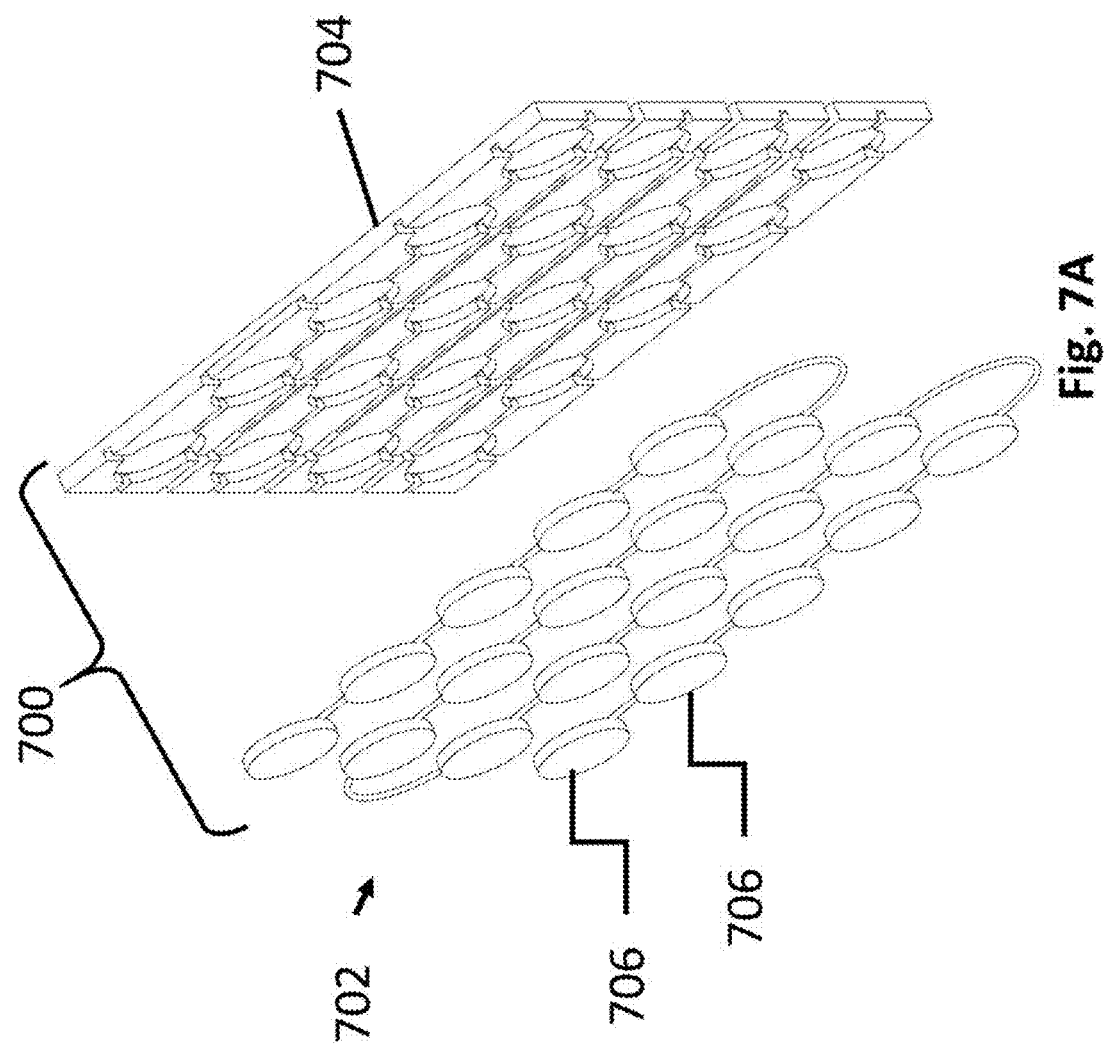
FIG. 7A illustrates an array of electrode elements arranged in selected physical locations.
Figure 7C:
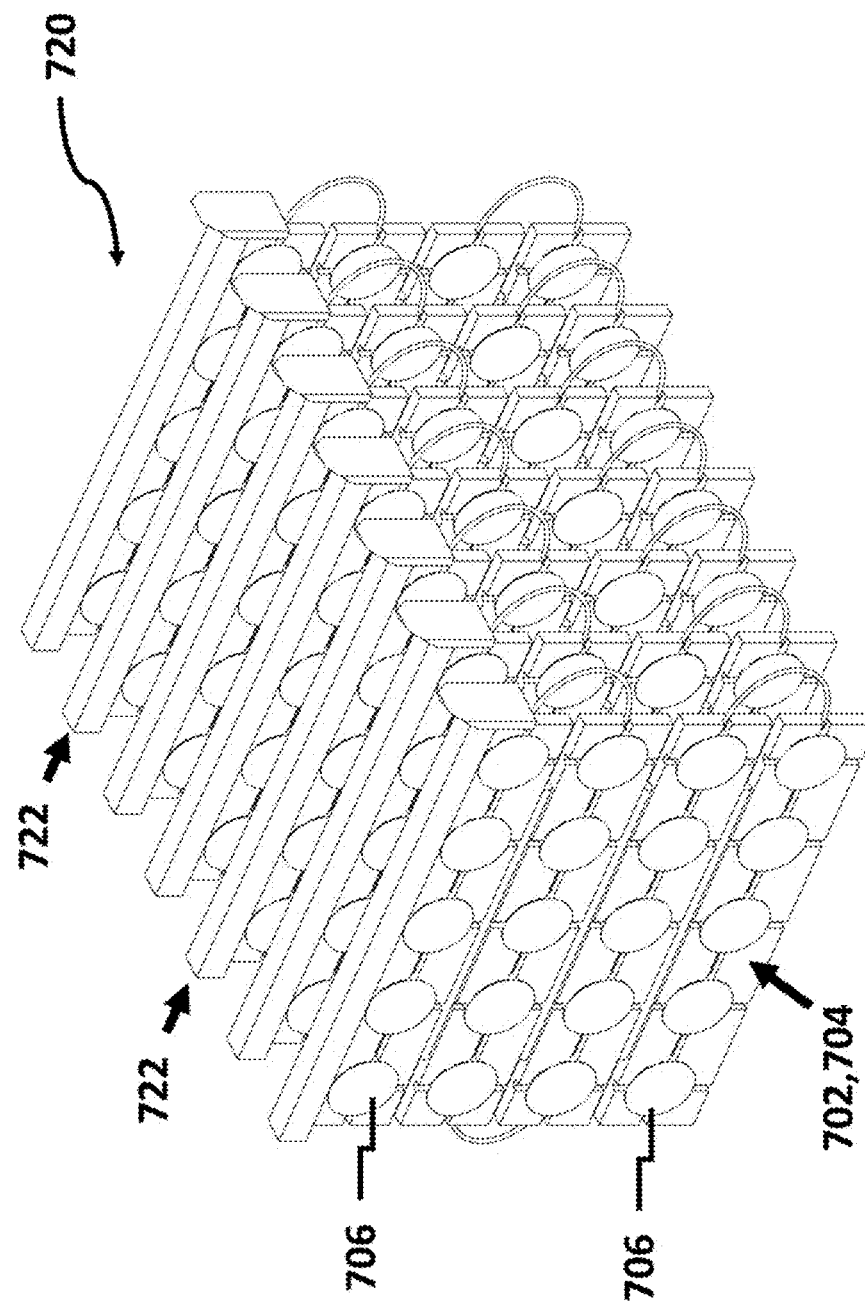
FIG. 7C illustrates multiple arrays of the electrode elements.
Figure 8:
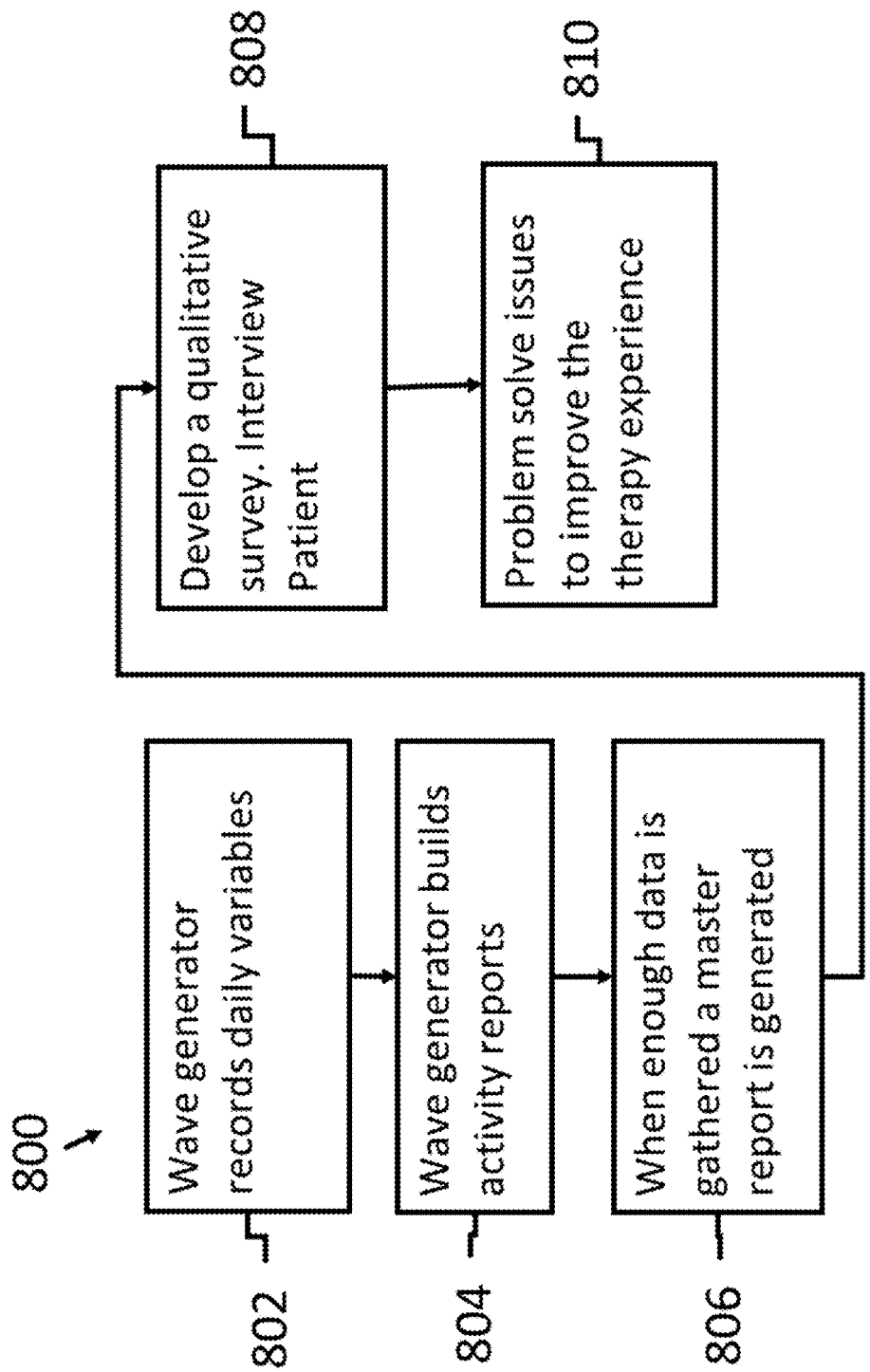
FIG. 8 illustrates another method of the present invention to modify the patient experience.

The best way to minimize the need for adjustments of array element placement is to place them correctly for each treatment—the first time before each day's treatment. Surprisingly this can be problematic due to changes in posture during the application, or movements made while array elements are being placed. These can cause incorrect starting positions which are then spread down the entire array. To minimize the likelihood of these type of problems the present invention includes an image marker system consisting of a small projector, floor markers and permanent or temporary tattoos. As illustrated in FIG. 6, a method 600 includes determining the patient's treatment posture at step 602; placing the array in an optimal position at step 604; applying at least 6 tattoo dots on the patient's body at step 606, 2 at shoulder level and one at the lower abdomen in the front, for example, and 3 on the back. At step 608 the patient is then positioned for a precision photograph. Floor markings are made to record foot placement. A precision image is made with camera distant, lens type and strength, etc., all recorded. A projector is then mounted in the correct position from the foot markings (step 610). Each day the patient steps (step 612) in front of the projector which projects on image (step 614) of the arrays onto the body. The patient repeatedly repositions (step 616) until the tattoo dots from the projected image line up with actual tattoos dots on the body. This lines up the image of the arrays to where they should be placed on the patient's body. The arrays are then placed using the image as a placement guide (step 618).

Now, additionally referring to FIGS. 7A-7D, one of the challenges of long term TTF therapy is patient compliance. Adding to the need to wear the device daily is the requirement of daily washing, drying and application of medical adhesive. To minimize the burden of this task our engineers have invented an apparatus 700 that accomplishes all three. A key component of the apparatus is a semi flexible portable holding rack 704 that is not only used to prepare for maintenance but is also used to re-secure the array elements 706 on the patient's body for the new day's therapy (not shown). For reapplying the arrays 702 the portable semi flexible rack 704 is held against the patient's body at the appropriate location and then gently bowed inward by pulling out on each side (not shown). The array elements 706 then pop out of the portable rack 704 and adhere to the patient's skin via the medical adhesive (not shown). An apparatus 710 is comprised of a chamber with a removable securing rack 718 that holds the flexible racks 720, movable application nozzles 734 that apply both water for washing and medical adhesive for skin adhering and drying fans 712, 714 and 716, and a drain for water removal. The apparatus 710 can be permanently mounted with a plumbed water supply and electric source (not shown). Perhaps near the household washer where both water, drain and electricity are available. At the end of each day's treatment the arrays are placed in the portable racks 722. The portable racks 722 are then placed in the securing racks. The securing rack is brought to the area where the TTF maintenance will be done. The securing rack with the arrays is then placed in the apparatus at 718, the door is closed and sealed. The system 710 is activated, with movable nozzles 734 controlled and programmed to move over the array elements 702 with ample warm water to remove the medical adhesive from the last therapy session. Once the array elements 706 are clean and the apparatus is drained, a drying sequence begins using imbedded fans 712, 714, 716. Once dry the arrays are allowed to sit to return to room temperature. The precision nozzles 734 then move over the discs 706 spraying them with the medical adhesive. The drying fans 712, 714, 716 are activated to dry the medical adhesive. The racks 720 containing the arrays can then be removed and placed conveniently wherever the patient puts on the arrays for the next day's treatment. In some configurations the apparatus is equipped with tanks 732 to hold medical adhesive, clean water and drainage water. In some configuration there are drain lines and supply lines form outside the apparatus 710.

As patients wear TTF behavior patterns emerge which can be used to improve care through qualitative research. Applicant has developed a process 800 whereby the wave generator controller (or computer) records daily activity (step 802), such as start and stop times, middle of the night interruptions, temperature readings, firing configuration, etc. The computer within the wave generator generates daily and weekly reports (step 804). When enough data is gathered a master, report is generated highlighting patterns of interruptions (step 806). The data is then used to create a qualitative survey (step 808) used to guide on interview with the patient. Interview questions like the following can be developed, "the report shows a repeated interruption of therapy between 4 am and 7 am most nights. Let me ask you what is problematic, or frustrated, or uncomfortable during that time period that makes you pause therapy?" The input from the patient can then be used to solve problems and hopefully improve therapy (step 810).

Figure 9A:
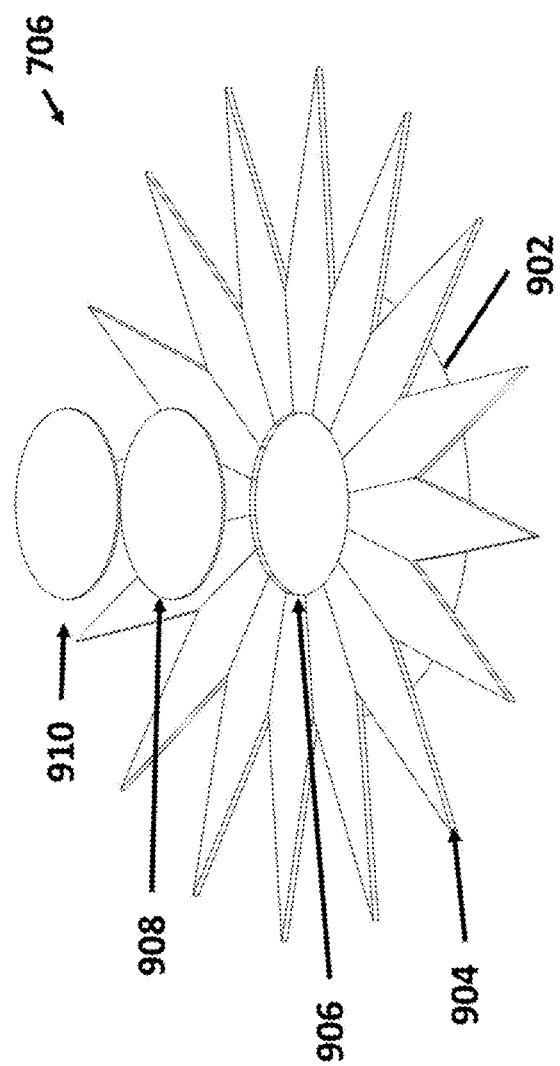
FIG. 9A illustrates the making of an electrode.

As previously mentioned one of the challenges of delivering TTF therapy is managing warmth on array elements. The goal is to keep the arrays as close to natural skin temperature as possible. Applicant's advanced form of TTF is has array elements 706 that are not exposed to open air, but instead have printed circuit boards on the non-skin side or a flex circuit, both of which hold the electronics required for dynamic reassignment of array elements. The printed circuit board or flex circuit is the then encapsulated with thermal conductive material. The layers of the array elements 706 then are as follows: Ceramic disc or material with conductive layer on one side, circuit board, thermal conductive potting material around the entire top of the element and the side as well, but not on the side that adheres to the patient's skin. The problem is that the warmth from the discs is trapped by the circuit board which is not thermally conductive. The warmth from the disc can only travel out the side up and around the circuit boards, causing a slow release or a bottleneck of warmth release. To combat this problem Applicant has developed a unique solution made of super thermally conductive, thin sheeting material. Some of these materials have 2 to 5 times the thermal conductivity of copper. This thin sheeting is cut into a star donut shape 904 with the body of the donut extending further out than the diameter of the hole. The diameter of the hole in the thermal conductive sheeting material is smaller than the diameter of the TTF array element with its conductive layer 908 and ceramic layer 910. The donut shape then has triangle shapes removed around its circumference. The tip of each removed triangle is facing the hole of the triangle, but does not reach the edge of the hole. The result is somewhat like a star shaped sheet of thermal conductive sheeting with a hole 906 in the middle. During construction of the array elements 706 the star shaped thermal sheeting 908 is centered on the flex circuit board in hole 906 under the ceramic array element 910. The hole in the middle allows current to energize the non-skin side of the ceramic to form the electric field for TTF. Once adhered the printed circuit board or flex circuit is mounted and secured to the disc 902. A thin coat of thermal conductive potting material is then used to encapsulate the array element (not shown). The extended points of the star shaped thermal sheeting are folded down and over the circuit board top coming together completely covering the array element (FIGS. 9B-9D). Then a final layer of thermal conductive potting material is used to cover the entire array element 706 (not shown). The result is an imbedded thermal conductive pathway for warmth to travel around the printed circuit board where it can be dissipated.

Figure 10A:
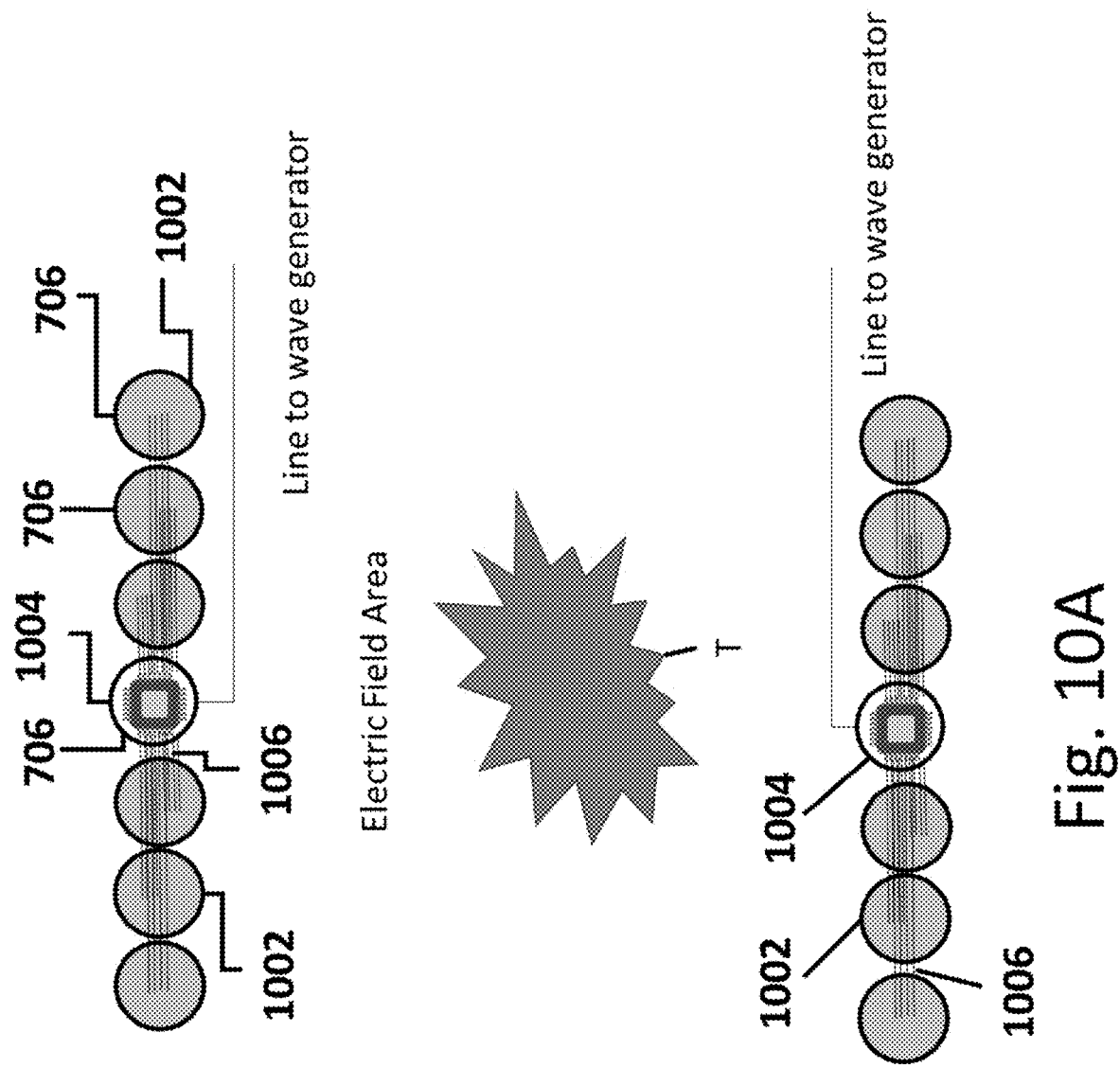
FIG. 10A illustrates a coupling of the field generator to a subarray of electrodes.

In yet another embodiment of the device the array elements 706 include both slave 1002 and fully dynamic 1004 electrodes, as illustrated in FIG. 10A. This can lower the cost of the overall array. In this embodiment each array element 706 is fully equipped with a microprocessor and all the added electronics described herein. In this embodiment the electronics, including, but not limited to sensors, LEDs, microprocessors, etc., are only placed on master elements 1004. These master elements 1004 then control slave elements 1002 through direct wires 1006 that supply power and sensory data. The masters 1004 control any number of slave 1002 array elements, for example, a row of 7 discs could have one master disc 1004 and then ample wires 1006 running to the 6 slave discs 1002. The master array element 1004 with its microprocessor would control the 6 slaves 1002 directing them to fire active or be a return. The slaves 1002 can extend in any direction from master disc 1004. The slaves 1002 may house limited sensors like a heat sensor connected by wire to the master 1004. FIG. 10B illustrates another distributed system where a master 1008, which may not be an electrode disc, controls slaves 1002.

In yet another embodiment of the present invention the controls 1106 associated with master elements described above and, on each disc, described in our patent are placed in the wave generator (also referred to herein as a field generator) 1102 to dynamically control rows 1104 of array elements rather than individual elements (as illustrated in FIG. 11). This embodiment offers economic benefit in cases where more granular control of individual elements is not needed as controls protected inside the wave generator 1102 should have a longer life.

A potential problem with delivering the most therapeutic portion of TTF at the most effective and safe intensities is the accidental occurrence of Peripheral Nerve Stimulation (PNS). This is not caused by any current but by the TT Field itself at higher levels of intensity. The occurrence of PNS can be unpredictable as each person has their own tolerance of the TT Fields. A large male may experience no PNS at higher intensities while a petite female may have considerable. The current solution to this problem is to throttle back the intensity of the TT Field eliminating the PNS, but this can sacrifice the most therapeutic level of TTF therapy. Applicant's solution is that the present invention turns off key array elements as PNS can sometimes only occur in certain spots where sensitive nerves are found. Another solution Applicant has noted that maintaining the same skin area coverage with smaller array elements is less likely to produce PNS without sacrificing intensity. This discovery led Applicant to create yet another embodiment. The master slave configuration described above is used to administer the needed the TT Field from a larger disc 1204 to smaller ones 1206 that total the same surface area. As illustrated in FIG. 12, Master elements 1202 control slave discs 1204, as should be understood as explained in this and previously filed applications between master 1202 and slave 1204 elements be accomplished through wireless methods.

In yet another embodiment further methods are employed to manage warming of the array elements. Fine microtubing is mounted between the ceramic disc and the printed circuit board, with each end of the tubing rising in a spiral fashion and then is connected to make one continuous loop. The spiral rises above the printed circuit board and is encapsulated in the thermal conductive potting material. Within the microtubing is a one-way valve that only allows fluid within the tubing to flow in one direction. As the fluid near the disc warms, it begins to flow upwards through the spiral cooling as it passes through the part of the spiral imbedded in the thermal conductive potting material. If required tiny fans can also be mounted on top of the discs to dissipate warmth. Alternatively, microtubing can be strung throughout the system. Instead of being in a closed loop on each disc. If tubing is strung throughout the system from disc to disc, the fluid within the system would be pumped through a cooling device and could be done so from multiple locations on the array.

Figure 13A:
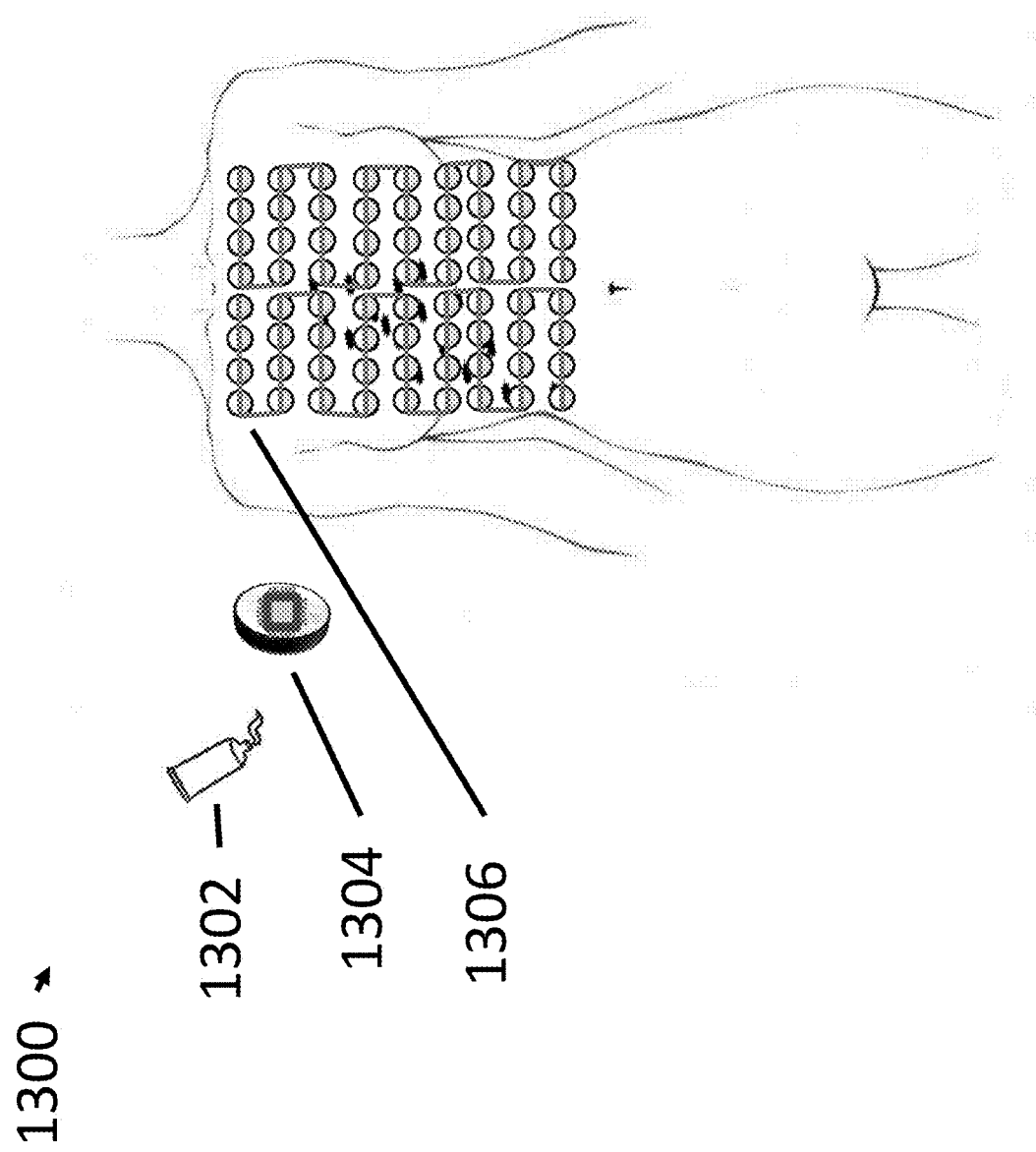
FIG. 13A illustrates one manner in which the electrodes are positioned on a torso of the patient.
Figure 13B:
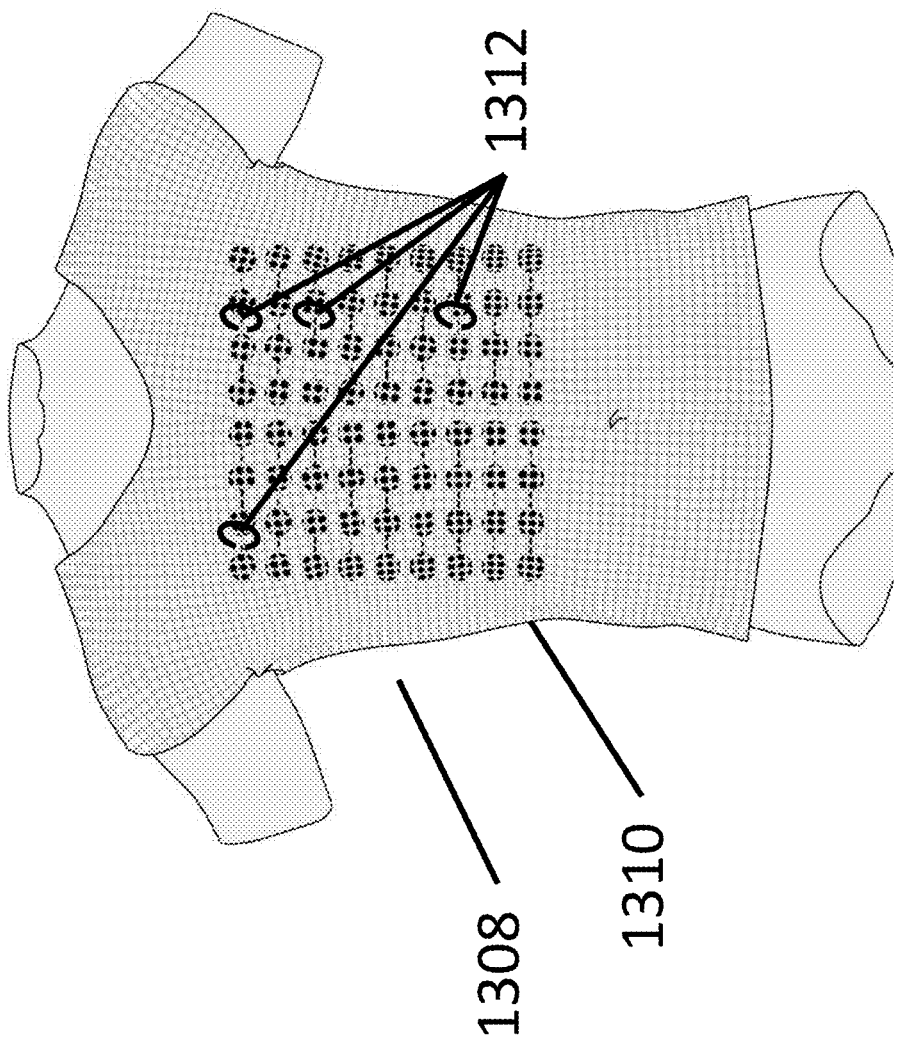
FIG. 13B illustrates the positioning of a garment with electrodes on a patient.

In all embodiments there is a need to hold the array elements directly on the patient's skin in such a way as to not interfere with electric field formation and to be comfortable for the patient. Applicant has a solution 1300 to the problem as shown in FIG. 13A. First a conductive medical adhesive 1302 (such as Tac-Gel), is placed on the patient side of the array element 1304. This is the insulated side from the silver layer. This is done on all elements in the entire array 1306. The array 1306 is then placed on the patient's skin via the applied medical adhesive 1302. Then a specially made stretchable shirt 1310 (usually with a zipper in the back), see FIG. 13B, is placed tightly over the arrays 1306 on the patient. Once zipped the shirt 1310 holds the arrays in place comfortably on torso 1308 of the patient. There are air holes through the fabric of the shirt to allow for cooling. To further secure the arrays in place and to prevent migration during sleep. Special clips 1312 made of material that will not interact with an electric field are placed through the shirt and around the connection wires/circuits between arrays.

In all embodiments the importance of preventing direct current from touching a patient's skin is of the utmost importance. The highest risk of a significant shock event would be if two array elements programmed for opposite polarities failed at the same time, allowing a breach of current to complete a circuit on, our through the skin. Although double insulation should prevent such a breach, Applicant has created a procedure 1400 (Refer to FIG. 14) designed to discover any breach before therapy begins. In our device each array element can be programmed to be either active or return. If a current breach to the skin were to occur while only one side of a polarity is open, the resulting circuit is minute only connecting with skin in the immediate area. The electric current is so small it is only felt as warmth on the skin. The present invention is able to detect even such small breaches. Testing all array elements for possible breaches while only one half of the polarity is open allows discovery and replacement of any compromised array elements before they are used in conjunction with an active and return for electric field formation. In procedure 1400, array elements are placed on the patient at step 1402. The array elements are then programmed to be energized with no return being selected at step 1404, then array elements are sequentially energized at step 1406 and detection of any leakage current is undertaken at step 1408, with leakage resulting in that element being disabled by the field generator. An LED on the offending electrode is activated to indicate a failed unit at step 1410. The failed unit is then removed and replaced with a functional electrode at step 1412.

Figure 15:
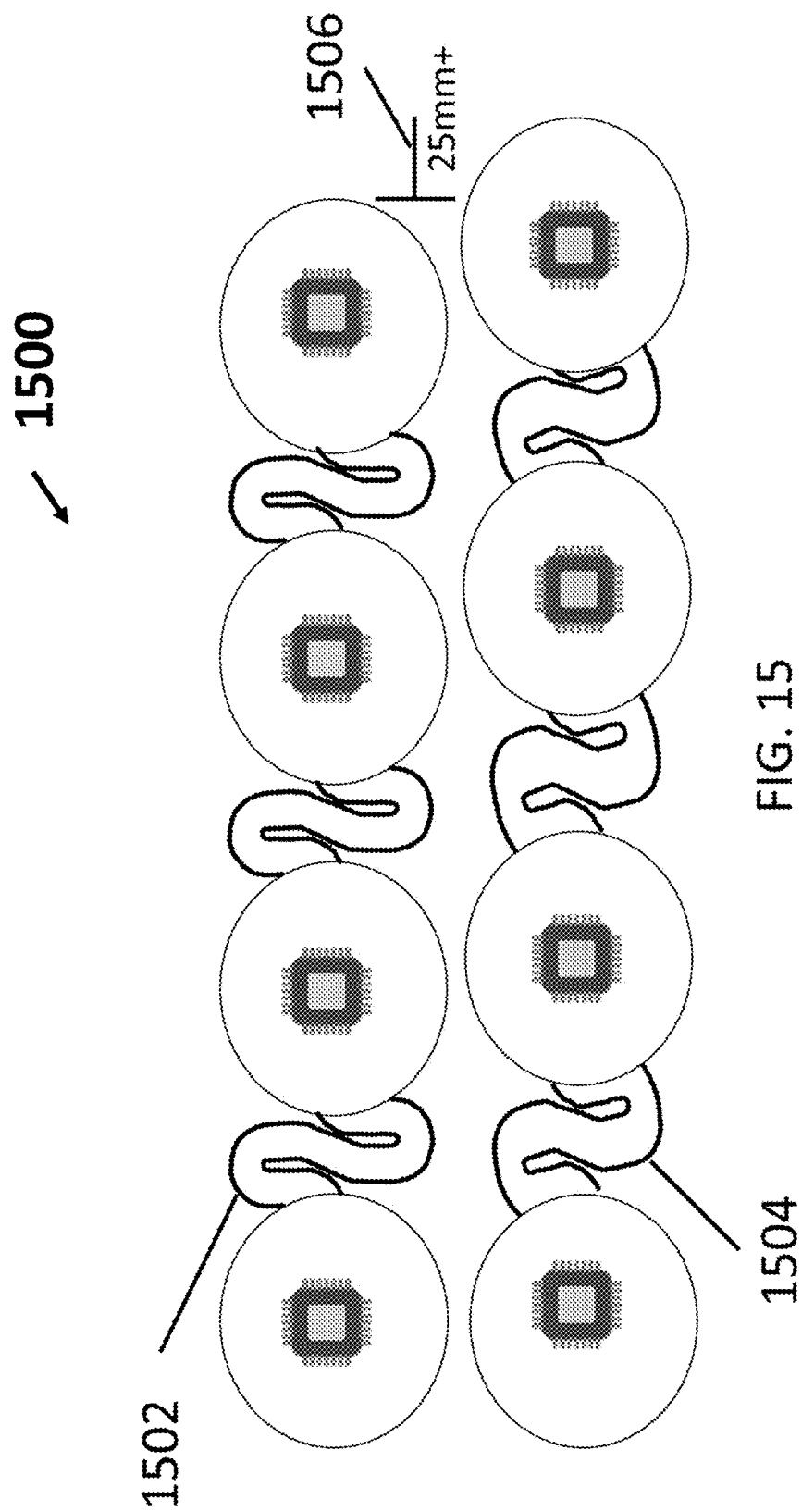
FIG. 15 illustrates an embodiment of a series of electrodes of the present invention having flexible wiring therebetween.

It is well known that in order for tumor treating field devices to be effective they must be worn for extended hours. Therefore, arrays that restrict movement and cause discomfort are not only undesirable, but can lower patient compliance to prescribed treatment. To minimize the degree to which arrays restrict movement, Applicant has developed a stretchable array 1500 by placing S shaped connectors 1502, 1504 between elements made of flex circuit as illustrated in FIG. 15. For example, when an array is placed on a person's back and they bend over or when they reach with their right hand to their left ear the surface area of the back expands. This causes pulling on conventional array connections. The flex circuit connectors 1502, 1504 in the shape of an S carry all needed wires and expand just enough to relieve pulling on areas that could cause discomfort. A row of array element discs connected in this way can provide 25 mm (as illustrated at 1506) or more of extra length when in the stretched position, increasing patient comfort.

Use of the term "array" herein has taken different meanings, dependent upon context. In one sense when talking about the grouping of electrodes on the body it is broadly referring to the physical rows and columns of the electrodes, or at least their placement, whether in rows and columns or not. The arrays that are used in forming electromagnetic fields are dynamically selected so that the desired field can be generated and this means a subset of the electrodes that may or may not be adjacent are selected and used.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and is claimed in the claims.

What is claimed is:

1. A method for delivering a plurality of electromagnetic fields to a body of an individual, comprising the steps of:
    positioning a plurality of electrode elements in a flexible rack that is configured to hold the electrode elements in predefined positions for application to the body of the individual;
    transferring the plurality of electrode elements from the flexible rack to the body of the individual;
    detecting temperatures of the plurality of electrode elements;
    determining alternate firing sequences of the plurality of electrode elements;
    implementing the determined alternate firing sequences for delivering the plurality of tumor treating electromagnetic fields and reducing temperatures of the plurality of electrode elements; and
    alternating electrode elements in the firing sequences based on a three-dimensional location of the electrode elements on the body, the location being established by the predefined positions of the electrode elements in the flexible rack, the electrode elements being secured to the body with an adhesive, the electrode elements that are selected for use in the alternate firing sequences maintain the electromagnetic field of at least 2V/cm in at least one of the tumors and using the detected temperature to control which of the electrode elements are chosen to maintain the electromagnetic field of at least 2V/cm.

2. The method of claim 1, wherein the step of implementing the determined alternate firing sequences is conducted by a control device coupled with the plurality of electrode elements, wherein the control device individually controls each electrode element for optimizing a duty cycle of each electrode element.

3. The method of claim 2, further including the steps of:
    turning on or off an individual electrode element, by the control device, while maintaining other electrode elements for maintaining an optimal field strength in a targeted area of a tumor; and
    passing a magnetic tool over at least one of the plurality of electrode elements to thereby enter or remove individual ones of the plurality of electrode elements to/from active duty by the control device.

4. The method of claim 2, wherein the step of detecting temperatures of the plurality of electrode elements includes sensing a temperature of a respective electrode element by a respective heat sensor connected to a respective electrode element of the plurality of electrode elements.

5. The method of claim 4, wherein the step of detecting temperatures of the plurality of electrode elements is conducted by the control device which receives the sensed temperatures of the plurality of electrode elements from a plurality of heat sensors.

6. The method of claim 5, wherein the step of determining alternate firing sequences of the plurality of electrode elements is conducted by the control device which determines alternate firing sequences in response to the sensed temperatures of the plurality of electrode elements.

7. The method of claim 2, wherein a plurality of switches are coupled with the plurality of electrode elements, wherein the control device conducts the step of implementing the determined alternate firing sequences by individually directing each electrode element to turn on or off by activating the plurality of switches.

8. The method of claim 2, further including a step of monitoring, by the control device, the implemented alternate firing sequences.

9. The method of claim 8, further including a step of selecting the implemented alternate firing sequences that optimizes therapeutic field intensities with optimal duty cycles on the plurality of electrode elements for continued implementation.

10. The method of claim 1, further including a step of assigning, by a control device, a first quantity of the plurality of electrode elements as phase A electrode elements and a second quantity of the plurality of electrode elements as phase B electrode elements, with the first quantity being different than the second quantity.

* * * * *